United States Patent
Berner et al.

(10) Patent No.: US 8,329,750 B2
(45) Date of Patent: *Dec. 11, 2012

(54) METHODS FOR TREATING VASOMOTOR SYMPTOMS USING GABA ANALOGS IN A GASTRIC RETENTIVE DOSAGE FORM

(75) Inventors: Bret Berner, Half Moon Bay, CA (US); Sui Yuen Eddie Hou, Foster City, CA (US); Theophilus J. Gana, Leesburg, VA (US); Marilou S. Cramer, Redwood City, CA (US); Carl A. Pelzel, Pleasanton, CA (US)

(73) Assignee: Depomed, Inc., Menlo Park, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 12/368,907

(22) Filed: Feb. 10, 2009

(65) Prior Publication Data

US 2009/0209645 A1 Aug. 20, 2009

Related U.S. Application Data

(60) Provisional application No. 61/065,442, filed on Feb. 11, 2008.

(51) Int. Cl.
*A61K 31/195* (2006.01)

(52) U.S. Cl. .......................... 514/561; 514/557; 514/554

(58) Field of Classification Search .................. None
See application file for complete search history.

(56) References Cited

U.S. PATENT DOCUMENTS

| | | | |
|---|---|---|---|
| 6,310,098 B1 | 10/2001 | Guttoso, Jr. | |
| 6,723,340 B2 | 4/2004 | Gusler et al. | |
| 7,438,927 B2 | 10/2008 | Berner et al. | |
| 2003/0091630 A1 | 5/2003 | Louie-Helm et al. | |
| 2003/0104062 A1 | 6/2003 | Berner et al. | |
| 2003/0200611 A1 | 10/2003 | Chaffee | |
| 2004/0259850 A1 | 12/2004 | Alves et al. | |
| 2005/0064036 A1* | 3/2005 | Berner et al. | 424/473 |
| 2006/0159743 A1 | 7/2006 | Berner et al. | |
| 2007/0184104 A1 | 8/2007 | Berner et al. | |

FOREIGN PATENT DOCUMENTS

| | | |
|---|---|---|
| WO | WO 03/035040 A1 | 5/2003 |
| WO | WO 2006/015294 A1 | 2/2006 |
| WO | WO 2007/079195 A1 | 7/2007 |
| WO | WO 2007/079195 A2 | 7/2007 |

OTHER PUBLICATIONS

International Search Report for PCT application PCT/US2009/033702, search report dated May 8, 2009, 4 pages (2009).
International Search Report and Written Opinion for PCT application PCT/US2009/033702, Search Report dated May 8, 2009, 14 pages (2009).
Loprinzi, C.L. et al., "Centrally active nonhormonal hot flash therapies", *The American Journal of Medicine*, 118(12B):118S-123S (2005).
Butt, D.A. et al., "Gabapendtin for the Treatment of Menopausal Hot Flashes: A Randomized Controlled Trial", *Menopause*, 15(2):310-818 (2008).
Canonico, M. et al. "Hormone replacement therapy and risk of venous thromboembolism in postmenopausal women: systematic review and meta-analysis", *BMJ Online*, 336(7655):1227-1231 (2008).
Guttoso, T. et al., "Gabapentin effects on hot flashes in postmenopausal women: A randomized controlled trial", *Obstetrics & Gynecology*, 101(2):337-345 (2003).
Loprinzi, C.L. et al., "Phase III trial of Gabapentin alone or in conjunction with an antidepressant in the management of hot flashes in women who have inadequate control with an antidepressant alone: NCCTG N03C5", *Journal of Clinical Oncology*, 25(3):308-312 (2007).
Knutson, K.L. et al., "Stability of the Pittsburgh Sleep Quality Index and the Epworth Sleepiness Questionnaires over 1 year in early middle-aged adults: the CARDIA study", *Sleep*, 29(11):1503-1506 (2006).
Mattar, C. N. et al., "Menopause, hormone therapy and cardiovascular and cerebrovascular disease", *Annals Academy of Medicine Singapore*, 37(1):54-62 (2008).
McGregor, J. and Shulman L.P, "Vasomotor Symptoms: Managing the Transition from Perimenopause to Postmenopause", *Supplemental to the Journal of Family Practice*, 57(10):S3-S21(2008).
Nelson, H.D. et al., "Nonhormonal Therapies for Menopausal Hot Flashes, Systematic Review and Meta-Analysis", *JAMA*, 295(17):2057-2071 (2006).
Pandya, K.J. et al., "Gabapentin for hot flashes in 420 women with breast cancer: a randomised double-blind placebo-controlled trial", *The Lancet*, 366(9488):818-824 (2005).
Reddy, S.Y. et al., "Gabapentin, estrogen, and placebo for treating hot flushes: a randomized controlled trial", *Obstetrics & Gynecology*, 108(1):41-48 (2006).

* cited by examiner

*Primary Examiner* — Brandon Fetterolf
*Assistant Examiner* — Theodore R West
(74) *Attorney, Agent, or Firm* — Judy M. Mohr; Paul Simboli; McDermott Will & Emery LLP

(57) ABSTRACT

Methods for treating vasomotor symptoms associated with menopause are described.

12 Claims, 9 Drawing Sheets

Subject's Initials _____ ID # _____ Date _____ Time _____ AM / PM

PITTSBURGH SLEEP QUALITY INDEX

INSTRUCTIONS:
The following questions relate to your usual sleep habits during the past month only. Your answers should indicate the most accurate reply for the majority of days and nights in the past month.
Please answer all questions.

1. During the past month, what time have you usually gone to bed at night?

BED TIME _____

2. During the past month, how long (in minutes) has it usually taken you to fall asleep each night?

NUMBER OF MINUTES _____

3. During the past month, what time have you usually gotten up in the morning?

GETTING UP TIME _____

4. During the past month, how many hours of actual sleep did you get at night? (This may be different than the number of hours you spent in bed.)

HOURS OF SLEEP PER NIGHT _____

*For each of the remaining questions, check the one best response. Please answer all questions.*

5. During the past month, how often have you had trouble sleeping because you . . .

a) Cannot get to sleep within 30 minutes

| Not during the past month _____ | Less than once a week _____ | Once or twice a week _____ | Three or more times a week _____ | b) Wake up in the middle of the night or early morning

| Not during the past month _____ | Less than once a week _____ | Once or twice a week _____ | Three or more times a week _____ | c) Have to get up to use the bathroom

| Not during the past month _____ | Less than once a week _____ | Once or twice a week _____ | Three or more times a week _____ |

Figure 1A d) Cannot breathe comfortably

Not during the          Less than           Once or twice       Three or more
past month_____         once a week_____    a week _____        times a week _____ e) Cough or snore loudly

Not during the          Less than           Once or twice       Three or more
past month_____         once a week_____    a week _____        times a week _____ f) Feel too cold

Not during the          Less than           Once or twice       Three or more
past month_____         once a week_____    a week _____        times a week _____ g) Feel too hot

Not during the          Less than           Once or twice       Three or more
past month_____         once a week_____    a week _____        times a week _____ h) Had bad dreams

Not during the          Less than           Once or twice       Three or more
past month_____         once a week_____    a week _____        times a week _____ i) Have pain

Not during the          Less than           Once or twice       Three or more
past month_____         once a week_____    a week _____        times a week _____ j) Other reason(s), please describe_____

How often during the past month have you had trouble sleeping because of this?

Not during the          Less than           Once or twice       Three or more
past month_____         once a week_____    a week _____        times a week _____

6. During the past month, how would you rate your sleep quality overall?

Very good _____
        Fairly good _____
        Fairly bad _____
        Very bad _____

Figure 1B

7. During the past month, how often have you taken medicine to help you sleep (prescribed or "over the counter?)

| Not during the past month _____ | Less than once a week _____ | Once or twice a week _____ | Three or more times a week _____ |

8. During the past month, how often have you had trouble staying awake while driving, eating meals, or engaging in social activity?

| Not during the past month _____ | Less than once a week _____ | Once or twice a week _____ | Three or more times a week _____ |

9. During the past month, how much of a problem has it been for you to keep up enough enthusiasm to get things done?

No problem at all    _____

Only a very slight problem    _____

Somewhat of a problem    _____

A very big problem    _____

10. Do you have a bed partner or room mate?

No bed partner or room mate    _____

Partner/room mate in other room    _____

Partner in same room, but not same bed    _____

Partner in same bed    _____

If you have a room mate or bed partner, ask him/her how often in the past month you have had . . .

a) Loud snoring

| Not during the past month _____ | Less than once a week _____ | Once or twice a week _____ | Three or more times a week _____ | b) Long pauses between breaths while asleep

| Not during the past month _____ | Less than once a week _____ | Once or twice a week _____ | Three or more times a week _____ | c) Legs twitching or jerking while you sleep

| Not during the past month _____ | Less than once a week _____ | Once or twice a week _____ | Three or more times a week _____ |

Figure 1C d) Episodes of disorientation or confusion during sleep

Not during the      Less than      Once or twice      Three or more
past month_____     once a week_____     a week _____     times a week _____ e) Other restlessness while you sleep; please describe
_____

Not during the      Less than      Once or twice      Three or more
past month_____     once a week_____     a week _____     times a week _____

*Buysse DJ, Reynolds CF, Monk TH, Berman SR, Kupfer DJ: Psychiatry Research, 28:193-213, 1989.*

Figure 1D

THE MENOPAUSE-SPECIFIC

QUALITY OF LIFE QUESTIONNAIRE

"MENQOL"

Primary Care Research Unit
Department of Family and Community Medicine
Sunnybrook and Women's College Health Sciences Centre
University of Toronto Copyright: John R. Hilditch, Jacqueline Lewis 1992

The development of this questionnaire was funded by CIBA-Geigy Canada Ltd., Mississauga, Canada This questionnaire may be used freely for research purposes. The authors request acknowledgement in any research publications in which the questionnaire is used.

First Revision June, 1996
Second Revision June, 1999

Figure 2A

INSTRUCTIONS

Each of the items in the questionnaire is in the form of the examples below:

| | | | Not at all bothered 0 | 1 | 2 | 3 | 4 | 5 | Extremely bothered 6 |
|---|---|---|---|---|---|---|---|---|---|
| NIGHT SWEATS | ☐ No | ☐ Yes → | ☐ 0 | ☐ 1 | ☐ 2 | ☐ 3 | ☐ 4 | ☐ 5 | ☐ 6 |

Indicate whether or not you have experienced this problem in the *last month*

IF YOU *HAVE NOT* EXPERIENCED THE PROBLEM:

Mark "No" ─────┐

| | | | | | | | | | |
|---|---|---|---|---|---|---|---|---|---|
| NIGHT SWEATS | ☑ No | ☐ Yes → | ☐ 0 | ☐ 1 | ☐ 2 | ☐ 3 | ☐ 4 | ☐ 5 | ☐ 6 |

└─────► Go to the next item.

IF YOU *HAVE* EXPERIENCED THE PROBLEM:

Mark "Yes", then check off how bothered you were by the problem.

| | | | | | | | | | |
|---|---|---|---|---|---|---|---|---|---|
| NIGHT SWEATS | ☐ No | ☑ Yes → | ☐ 0 | ☐ 1 | ☑ 2 | ☐ 3 | ☐ 4 | ☐ 5 | ☐ 6 |

└─────► Go to the next item.

This questionnaire is completely confidential. Your name will not be associated with your responses. However, if for any reason you do not wish to complete an item, please leave it and go on to the next one.

Figure 2B

For each of the following items, indicate whether you have experienced the problem in the PAST MONTH. If you have, rate how much you have been *bothered* by the problem.

|    |                                 |     |     |   | Not at all bothered 0 | 1 | 2 | 3 | 4 | 5 | Extremely bothered 6 |
|----|---------------------------------|-----|-----|---|---|---|---|---|---|---|---|
| 1. | HOT FLUSHES OR FLASHES          | ☐ No | ☐ Yes | → | ☐ 0 | ☐ 1 | ☐ 2 | ☐ 3 | ☐ 4 | ☐ 5 | ☐ 6 |
| 2. | NIGHT SWEATS                    | ☐ No | ☐ Yes | → | ☐ 0 | ☐ 1 | ☐ 2 | ☐ 3 | ☐ 4 | ☐ 5 | ☐ 6 |
| 3. | SWEATING                        | ☐ No | ☐ Yes | → | ☐ 0 | ☐ 1 | ☐ 2 | ☐ 3 | ☐ 4 | ☐ 5 | ☐ 6 |
| 4. | DISSATISFACTION WITH MY PERSONAL LIFE | ☐ No | ☐ Yes | → | ☐ 0 | ☐ 1 | ☐ 2 | ☐ 3 | ☐ 4 | ☐ 5 | ☐ 6 |
| 5. | FEELING ANXIOUS OR NERVOUS      | ☐ No | ☐ Yes | → | ☐ 0 | ☐ 1 | ☐ 2 | ☐ 3 | ☐ 4 | ☐ 5 | ☐ 6 |
| 6. | POOR MEMORY                     | ☐ No | ☐ Yes | → | ☐ 0 | ☐ 1 | ☐ 2 | ☐ 3 | ☐ 4 | ☐ 5 | ☐ 6 |
| 7. | ACCOMPLISHING LESS THAN I USED TO | ☐ No | ☐ Yes | → | ☐ 0 | ☐ 1 | ☐ 2 | ☐ 3 | ☐ 4 | ☐ 5 | ☐ 6 |
| 8. | FEELING DEPRESSED, DOWN OR BLUE | ☐ No | ☐ Yes | → | ☐ 0 | ☐ 1 | ☐ 2 | ☐ 3 | ☐ 4 | ☐ 5 | ☐ 6 |
| 9. | BEING IMPATIENT WITH OTHER PEOPLE | ☐ No | ☐ Yes | → | ☐ 0 | ☐ 1 | ☐ 2 | ☐ 3 | ☐ 4 | ☐ 5 | ☐ 6 |
| 10. | FEELINGS OF WANTING TO BE ALONE | ☐ No | ☐ Yes | → | ☐ 0 | ☐ 1 | ☐ 2 | ☐ 3 | ☐ 4 | ☐ 5 | ☐ 6 |
| 11. | FLATULENCE (WIND) OR GAS PAINS | ☐ No | ☐ Yes | → | ☐ 0 | ☐ 1 | ☐ 2 | ☐ 3 | ☐ 4 | ☐ 5 | ☐ 6 |
| 12. | ACHING IN MUSCLES AND JOINTS   | ☐ No | ☐ Yes | → | ☐ 0 | ☐ 1 | ☐ 2 | ☐ 3 | ☐ 4 | ☐ 5 | ☐ 6 |
| 13. | FEELING TIRED OR WORN OUT      | ☐ No | ☐ Yes | → | ☐ 0 | ☐ 1 | ☐ 2 | ☐ 3 | ☐ 4 | ☐ 5 | ☐ 6 |
| 14. | DIFFICULTY SLEEPING            | ☐ No | ☐ Yes | → | ☐ 0 | ☐ 1 | ☐ 2 | ☐ 3 | ☐ 4 | ☐ 5 | ☐ 6 |
| 15. | ACHES IN BACK OF NECK OR HEAD  | ☐ No | ☐ Yes | → | ☐ 0 | ☐ 1 | ☐ 2 | ☐ 3 | ☐ 4 | ☐ 5 | ☐ 6 |
| 16. | DECREASE IN PHYSICAL STRENGTH  | ☐ No | ☐ Yes | → | ☐ 0 | ☐ 1 | ☐ 2 | ☐ 3 | ☐ 4 | ☐ 5 | ☐ 6 |

Figure 2C

|     |                                                          |     |     |   | Not at all bothered 0 | 1 | 2 | 3 | 4 | 5 | Extremely bothered 6 |
| --- | -------------------------------------------------------- | --- | --- | - | --- | --- | --- | --- | --- | --- | --- |
| 17. | DECREASE IN STAMINA | ☐ No | ☐ Yes | → | ☐ 0 | ☐ 1 | ☐ 2 | ☐ 3 | ☐ 4 | ☐ 5 | ☐ 6 |
| 18. | LACK OF ENERGY | ☐ No | ☐ Yes | → | ☐ 0 | ☐ 1 | ☐ 2 | ☐ 3 | ☐ 4 | ☐ 5 | ☐ 6 |
| 19. | DRY SKIN | ☐ No | ☐ Yes | → | ☐ 0 | ☐ 1 | ☐ 2 | ☐ 3 | ☐ 4 | ☐ 5 | ☐ 6 |
| 20. | WEIGHT GAIN | ☐ No | ☐ Yes | → | ☐ 0 | ☐ 1 | ☐ 2 | ☐ 3 | ☐ 4 | ☐ 5 | ☐ 6 |
| 21. | INCREASED FACIAL HAIR | ☐ No | ☐ Yes | → | ☐ 0 | ☐ 1 | ☐ 2 | ☐ 3 | ☐ 4 | ☐ 5 | ☐ 6 |
| 22. | CHANGES IN APPEARANCE, TEXTURE OR TONE OF MY SKIN | ☐ No | ☐ Yes | → | ☐ 0 | ☐ 1 | ☐ 2 | ☐ 3 | ☐ 4 | ☐ 5 | ☐ 6 |
| 23. | FEELING BLOATED | ☐ No | ☐ Yes | → | ☐ 0 | ☐ 1 | ☐ 2 | ☐ 3 | ☐ 4 | ☐ 5 | ☐ 6 |
| 24. | LOW BACKACHE | ☐ No | ☐ Yes | → | ☐ 0 | ☐ 1 | ☐ 2 | ☐ 3 | ☐ 4 | ☐ 5 | ☐ 6 |
| 25. | FREQUENT URINATION | ☐ No | ☐ Yes | → | ☐ 0 | ☐ 1 | ☐ 2 | ☐ 3 | ☐ 4 | ☐ 5 | ☐ 6 |
| 26. | INVOLUNTARY URINATION WHEN LAUGHING OR COUGHING | ☐ No | ☐ Yes | → | ☐ 0 | ☐ 1 | ☐ 2 | ☐ 3 | ☐ 4 | ☐ 5 | ☐ 6 |
| 27. | DECREASE IN MY SEXUAL DESIRE | ☐ No | ☐ Yes | → | ☐ 0 | ☐ 1 | ☐ 2 | ☐ 3 | ☐ 4 | ☐ 5 | ☐ 6 |
| 28. | VAGINAL DRYNESS | ☐ No | ☐ Yes | → | ☐ 0 | ☐ 1 | ☐ 2 | ☐ 3 | ☐ 4 | ☐ 5 | ☐ 6 |
| 29. | AVOIDING INTIMACY | ☐ No | ☐ Yes | → | ☐ 0 | ☐ 1 | ☐ 2 | ☐ 3 | ☐ 4 | ☐ 5 | ☐ 6 |

Figure 2D

INSTRUCTIONS FOR THE USE AND SCORING OF THE MENOPAUSE-SPECIFIC QUALITY OF LIFE QUESTIONNAIRE

USE:

1. This questionnaire is designed to be self-administered, either in person or by mail.

2. Specific instructions for the subject are part of the instrument.

3. The questionnaire requires, on average, 7 minutes to complete, with a range of 5 to 15 minutes.

4. The questionnaire is appropriate for English-speaking subjects.

5. The psychometric properties are based on data collection periods one month apart.

6. The questionnaire was developed using data from women who:

a) were between the ages of 47 and 62 years
    b) were 2 to 7 years post-menopause
    c) had a uterus
    d) had not been on hormone replacement therapy in the past 6 months.

Figure 2E

METHODS FOR TREATING VASOMOTOR SYMPTOMS USING GABA ANALOGS IN A GASTRIC RETENTIVE DOSAGE FORM

CROSS-REFERENCE TO RELATED APPLICATIONS

This application claims priority under 35 U.S.C. 119(e) to the U.S. Provisional Application No. 61/065,442, filed Feb. 11, 2008, the entire content of which is hereby incorporated by reference.

TECHNICAL FIELD

The present subject matter relates to methods of treating a vasomotor symptom using gastric retentive dosage forms comprising a gamma-aminobutyric acid (GABA) analog. In a preferred embodiment, a method for treating one or more menopause-related vasomotor symptoms is provided.

BACKGROUND

Vasomotor symptoms of hot flashes, hot flushes, and night sweats are probably best known as being associated with female menopause. These vasomotor symptoms affect an estimated 75% of women aged over 50 years. However, these vasomotor symptoms may also be experienced, for example, by women undergoing breast cancer treatment with the anti-estrogen drug tamoxifen, by women who have had pituitary failure and do not secrete luteinizing hormone and follicular stimulating hormone, and by men who are undergoing androgen deprivation therapy following a bilateral orchiectomy or treatment with gonadotrophin-releasing-hormone agonist for metastatic prostate cancer.

Hot flashes are manifested as an increase in skin temperature, and are often accompanied by a sudden onset of sweating on the face, neck and chest. Hot flashes significantly affect the quality of life for those who experience them, and are particularly bothersome at night as they can disturb sleep, leading to fatigue and lack of productivity during the day. While hot flashes are commonly associated with females in a perimenopausal or menopausal state of life, they are not, however, unique to menopause. Hot flashes can be caused by a variety of conditions, including thyroid disease, infection, epilepsy, insulinoma, carcinoid syndromes, leukemia, pulmonary tuberculosis, pancreatic tumors, autoimmune disorders, and mast cell disorders. Hot flashes may occur in women diagnosed with cancer or other diseases treated by chemotherapy, wherein there is a temporary or permanent side effect on the ovaries. Hot flashes generally last several minutes and are evidenced by a visible flushing of the skin. Often dizziness, palpitations and diaphoresis accompany a hot flash episode.

Currently, a preferred treatment for hot flashes in patients is hormone replacement therapy either using estrogen and progesterone or estrogen-replacement therapy. Unfortunately, these hormone therapies are inappropriate for patients previously diagnosed with breast cancer, as either estrogen or progesterone may be associated with an increased risk of cancer recurrence and are known to specifically promote growth of breast cancer cell with estrogen receptors. Estrogen may also increase the risk of coronary and thromboembolic events during the first year of treatment. Although the use of low dose estradiol therapy may diminish the risk for these large specialized patient populations, the risks of estrogen therapy are still great.

There are numerous non-hormonal remedies commonly used by women suffering hot flashes including, for example, isoflavone, black cohosh, vitamin E, and the antidepressants fluoxetine, paroxetine, and venlafaxine. However, efficacy of these remedies is less than that of the hormone replacement therapies.

The gamma-aminobutyric acid (GABA) analog gabapentin is approved in the United States for use in treating epilepsy and post-herpetic neuralgia, in immediate-release tablets and capsules. The drug administered in immediate release dosage forms is also being studied for use in reducing both the frequency and severity of hot flashes (Butt D. A. et al., *Menopause*, 2008:15(2):310-318; Reddy S. Y. et al., *Obstetrics & Gyn.*, 2006:108(1):41-48; Pandya K. J. et al., *Lancet*, 2005: 366(9488):818-824; Loprinzi C. L. et al., *J. Clin. Oncology*, 2007:25(3):308-312; U.S. Pat. No. 6,310,098).

When used in studies to assess effectiveness in the treatment of hot flashes, immediate release gabapentin forms require administration three times per day (t.i.d.), and result in undesired side effects. Side effects reported from use of immediate release gabapentin products include, most commonly, somnolence and dizziness, and to a lesser degree, fatigue, ataxia, weight gain, peripheral edema, diarrhea, headache, dry mouth, and blurred vision. More recently, gabapentin use has been associated with the serious side effect of reversible visual field constriction (Bekkelund et al., *Brit Med. J* 323:1193 (2006)). In studies involving use of gabapentin to treat menopausal symptoms, the prevalence of somnolence and dizziness side effects resulted in many women discontinuing use of the drug.

The need for t.i.d. dosing and unwanted side effects associated with immediate release gabapentin dosage forms may contribute to poor compliance for some patients in need of relief from vasomotor symptoms. The above described side effects in this generally healthy population can be a considerable barrier to compliance with gabapentin therapy. In this respect, controlled release dosage forms that would lower the number of daily dosings of gabapentin to once-daily (qd) or twice-daily (b.i.d.) dosings, particularly without a mid-day dose, would provide significant advantage over the conventional immediate release dosage forms.

The need for t.i.d. dosing is due partially to the fact that there is a decrease in bioavailability with increasing dose of the immediate release dosage form of gabapentin. This is attributed to partially carrier-mediated absorption (Stewart et al., *Pharmaceutical Research*, 1993, 10(2):276-281; Bourgeois, *Epliepsia*, 36 (Suppl. 5):S1-S7 (1995); Gram, *Epliepsia*, 37 (Suppl. 6):S12-S16 (1996); *Drugs of Today*, 31:613-9:975-82 (1995); *Neurology*, 44(Suppl. 5): S17-S32 (2003)). Overcoming poor bioavailability properties requires sustained exposure of the small intestine to gabapentin. Sustained-release formulations of gabapentin that provide prolonged exposure to the small intestine have successfully been formulated as gastric retentive dosage forms. These dosage forms are illustrated, for example, in U.S. Pat. Nos. 6,723,340 and 7,438,927, and U.S. Patent Publication Nos. 2003/0091630, 2003/0200611, and 2007/0184104. Gastric retentive dosage forms as described in these patents and patent publications are formulated to be retained in the stomach when taken with food, i.e., in a fed mode. Gastric retention is achieved either through the imbibition of fluid and resultant swelling upon administration or through design of a dosage form that has a size, prior to administration, which is sufficient for gastric retention in a fed mode. As a result, the gabapentin is slowly released in the stomach over time, upstream of the small intestine where gabapentin absorption is maximal.

Despite slow release of gabapentin, minimization of intolerable side effects of gabapentin requires that doctors titrate patients slowly to a maintenance dose. This titration period can take weeks or even a month. The complexity and length of the titration regimen may result in prematurely discontinuing therapy by patients prior to reaching the maintenance dose or to doctors preferring other therapeutic options.

In order for gabapentin and other GABA analogs, in particular pregabalin, to gain widespread acceptance for use to treat vasomotor symptoms due to diverse causes, and particularly due to hormonal changes before and during menopause, there is a need for a dosing regimen that facilitates patient compliance and reduces and/or eliminates adverse side effects. Treatment methods effective in ameliorating, preventing or attenuating vasomotor symptoms are needed, particularly for subjects contraindicated for other accepted treatments, such as hormone replacement therapy and estrogen replacement therapy, or who do not wish to take on the risks associated with these treatments.

BRIEF SUMMARY

The following aspects and embodiments thereof described and illustrated below are meant to be exemplary and illustrative, not limiting in scope.

In one aspect a method for improving sleep quality in a subject, such as a female subject, experiencing menopause-related vasomotor symptoms by administering a GABA analog, such as gabapentin, pregablin or a prodrug of gabapentin in a gastric retentive dosage form is provided. In some embodiments, sleep quality is measured by the Pittsburgh Quality Sleep Index (PQSI). In some embodiments, administration of gabapentin in a gastric retentive dosage form reduces daytime somnolence in a subject relative to a subject untreated with a gastric retentive dosage form of gabapentin. In some embodiments, a subject treated with a gastric retentive dosage form comprising gabapentin experiences reduced daytime somnolence relative to a subject treated with an immediate release dosage form comprising gabapentin. In some embodiments, the subject is a female.

In another aspect, a method is provided for improving compliance with gabapentin treatment in a subject experiencing and/or diagnosed with a vasomotor symptom. The method comprises administering gabapentin in a gastric retentive dosage form. In one embodiment, administration of a gastric retentive dosage form comprising gabapentin reduces one or more side effects experienced by a subject associated with an immediate release gabapentin dosage form. In some embodiments, the subject is a female.

In yet another aspect a method for treating a female who has been post-menopausal for at least one year, preferably at least two years and is experiencing vasomotor symptoms is provided. The method comprises administering a gastric retentive dosage form comprising a GABA analog, such as gabapentin, pregablin or a prodrug of gabapentin.

In still another aspect a method for treating a female who is experiencing vasomotor symptoms of menopause and who is or may be at risk of cardiovascular disease, by administering a gastric retentive dosage form comprising a GABA analog, such as gabapentin, pregablin or a prodrug of gabapentin, is provided.

In another aspect a method for treating a female experiencing menopause-related vasomotor symptoms and who is contraindicated for hormone-replacement therapy is provided. The method comprises administering a gastric retentive dosage form comprising gabapentin. In some embodiments, the female experiencing menopausal vasomotor symptoms has been diagnosed with, or is being or has been treated for breast cancer.

In still another aspect, a dose regimen for treating a female experiencing menopause-related vasomotor symptoms is provided. The method comprises administering a first total daily dose of gabapentin in a gastric retentive dosage form for a first period of time, administering a second total daily dose of gabapentin, wherein the second dose is greater than the first dose, for a second period of time, and administering a third total daily dose for a third period of time, to reduce the frequency and/or severity of vasomotor symptoms.

In some embodiments, the third total daily dose is equal to the second total daily dose. In some embodiments, the third total daily dose is greater than the second total daily dose. In some embodiments, the third total daily dose is less than the second total daily dose.

In some embodiments, the first total daily dose is between about 100 to about 1800 mg. In some embodiments, the first total daily dose is between about 300 and about 1200 mg. In some embodiments, the first total daily dose is between about 600 and about 1200 mg. In some embodiments, the first total daily dose is about 600 mg. In some embodiments, the first total daily dose is about 1200 mg. In some embodiments, the first total daily dose is about 1500 mg. In some embodiments, the first total daily dose is about 1800 mg.

In some embodiments, the second total daily dose is between about 600 and 1800 mg. In some embodiments, the second total daily dose is between about 800 and 1500 mg. In some embodiments, the second total daily dose is about 600 mg. In some embodiments, the second total daily dose is about 1200 mg. In some embodiments, the second total daily dose is about 1800 mg.

In some embodiments, the third total daily dose is between about 600 and about 2400 mg. In some embodiments, the third total daily dose is between about 900 mg and about 1800 mg. In some embodiment, the third total daily dose is about 1800 mg. In some embodiments, the third total daily dose is about 1200 mg. In some embodiments, the third total daily dose is about 600 mg.

In some embodiments, the first total daily dose is about 600 mg and the second total daily dose is about 1200 mg.

In some embodiments, the first total daily dose is about 1200 mg and the second total daily dose is about 600 mg.

In some embodiments, the first total daily dose is about 600 mg and the second total daily dose is about 600 mg.

In some embodiments, the first total daily dose is about 600 mg and the second total daily dose is about 1800 mg.

In some embodiments, the first total daily dose is about 1200 mg and the second total daily dose is about 1200 mg In some embodiments, the first time period is about one to three days. In some embodiments, the first time period is one, two, or three days.

In some embodiments, the second time period is between about two and four days. In some embodiments, the second time period is two, three, or four days.

In some embodiments, the third time period is two or more days.

In some embodiments, the first total daily dose is about 600 mg and is administered once per day with an evening meal. In some embodiments, the second total daily dose is about 1200 mg and is administered once per day with an evening meal.

In some embodiments, the third total daily dose is about 600 mg per day and is administered with an evening meal. In some embodiments, the third total daily dose is about 1200 mg per day and is administered with an evening meal. In some embodiments, the third total daily dose is 1800 mg per day wherein a 1200 mg dose of gabapentin is administered with an evening meal and a 600 mg dose of gabapentin is administered with a morning meal.

In any one of the above methods, one embodiment is a gastric retentive dosage form comprised of a dose of gabapentin and a hydrophilic swellable polymer, wherein the dosage form after administration swells to a size that is retained in the stomach in fed mode.

In some embodiments, the gastric retentive dosage form is comprised of a single, solid polymeric matrix that swells unrestrained dimensionally in the presence of water, and that remains substantially intact when swollen, for release of a GABA analog by erosion, diffusion, or a combination of erosion and diffusion.

In some embodiments, the gastric retentive dosage form comprises a GABA analog. In another embodiment, the GABA analog is pregabalin.

In some embodiments, the gastric retentive dosage form is administered once per day. In another embodiment, the gastric retentive dosage form is administered two times per day.

In some embodiments, the gastric retentive dosage form is administered in both a morning dose and an evening dose. In some embodiments, the morning dose is equal to the evening dose. In some embodiments, the morning dose is less than the evening dose. In some embodiments, the morning dose is equal to or less than about one-half of the evening dose. In some embodiments, the morning dose is equal to or less than about one-third of the evening dose. In some embodiments, the morning dose is equal to or less than about one-quarter of the evening dose.

In some embodiments, the gastric retentive dosage form is administered with a morning meal. In some embodiments, the gastric retentive dosage form is administered with an evening meal. In some embodiments, the gastric retentive dosage form is administered to a subject in a fed mode.

In some embodiments, the subject is a male, and in other embodiments the subject is a female.

In some embodiments, the vasomotor symptom is a hot flash. In one embodiment, the method is effective to delay the onset of a hot flash, reduce the frequency of hot flashes, and/or decrease the severity of hot flashes.

In some embodiments, the subject is experiencing vasomotor symptoms associated with menopause. In some embodiments, menopause has occurred naturally. In some embodiments, menopause was induced through surgery, chemotherapy, or pelvic radiation.

In some embodiments, the subject is experiencing vasomotor symptoms not associated with menopause. In some embodiments, the subject is experiencing vasomotor symptoms caused by thyroid disease, infection, epilepsy, insulinoma, carcinoid syndromes, leukemia, pulmonary tuberculosis, pancreatic tumors, autoimmune disorders, or mast cell disorders.

In some embodiments, the subject is a male experiencing hot flashes resulting hormone therapy administered to treat prostate cancer.

In some embodiments, a subject being administered a gastric retentive dosage form comprising gabapentin experiences fewer and/or less severe side effects as compared to a subject taking an immediate release dosage form comprising an equivalent dose of gabapentin. In some embodiments, the fewer and/or less severe side effects include one or more side effects selected from somnolence, dizziness, coordination problems, infections, fever, nausea or vomiting, edema, unusual eye movements, double vision or blurred vision, weakness or fatigue, diarrhea or constipation, dry mouth, increased appetite or weight gain, bronchitis, sore throat, mentation, nervousness, speech problems, memory loss, indigestion or heartburn, gas, back pain, problems walking, twitching, high blood sugar, conjunctivitis, ear infection and loss of hearing.

In addition to the exemplary aspects and embodiments described above, further aspects and embodiments will become apparent by reference to the drawings and by study of the following descriptions.

BRIEF DESCRIPTION OF THE DRAWINGS

FIGS. 1A-1D show the Pittsburgh Sleep Quality Index (PSQI) questionnaire provided to clinical subjects.

FIGS. 2A-2E show the Menopause-Specific Quality of Life Questionnaire (MENQOL) questionnaire provided to clinical subjects.

DETAILED DESCRIPTION

I. Definitions

A "hot flash" refers to a recurrent, transient sensation ranging from warmth to intense heat on the upper body and/or face typically associated with flushing that spreads over the body, and sometimes accompanied by perspiration, and sometimes followed by chills. Night sweats are hot flashes that occur with perspiration during sleep.

A "hot flush" refers to an involuntary skin redness usually of the face. In a preferred embodiment, a hot flush intends an involuntary skin redness of the face due to a hot flash.

"Menopause" is defined as the permanent cessation of ovulation and menstruation. Menopause is diagnosed after 12 consecutive months of amenorrhea that is not associated with either a physiological or pathological cause. Menopause may also be diagnosed by measuring levels of follicle stimulating hormone (FSH) in the blood. As used herein, menopause intends menopause associated with natural changes in female hormonal levels, drug-induced menopause (such as by anti-estrogen or anti-androgen therapy) and/or surgically induced menopause (such as by hysterectomy, oopherectomy, orchiectomy, chemotherapy, radiation of the pelvis, or any process that impairs ovarian blood supply). Symptoms of menopause include, but are not limited to, vasomotor symptoms, irregular menstrual cycles, nervousness, excitability, fatigue, neurobehavioral slowing, apathy, mental depression, vaginal dryness and/or atrophy, and/or impairment of short term memory.

"Perimenopause" refers to the beginning stages of menopause when physical symptoms associated with menopause are present, yet before cessation of menstrual cycles for a period of a year. Perimenopause may be a period of a few months to several years, and up to 15 years before menopause. That is, perimenopause may occur in a female between 45 to 50 years of age, between 40 to 50 years of age, or between 35 to 50 years of age. Perimenopause can be divided into two phases. Early menopausal transition is characterized by increases in menstrual cycle length greater than seven days, whereas late menopausal transition refers to a period of at least two skipped menstrual cycles and at least one period of amenorrhea exceeding sixty days.

"Premature menopause" refers to an onset of symptoms of menopause at an age medically considered too young for natural menopause. Presentation of one or more menopausal symptoms in a female under the age of about 40 may be associated with premature menopause, and can be confirmed for example by measuring blood estradiol and/or FSH levels, where an estradiol level under a certain concentration or an FSH blood level above a certain concentration is/are an indication of ovarian failure and premature menopause.

"Postmenopause" is defined as the time after which a female has experienced twelve consecutive months of amenorrhea (lack of menstruation).

"Vasomotor symptoms" (VMS) refers to a physical presentation due to an action upon a blood vessel which alters its diameter, as vasodilation or vasoconstriction. Vasomotor symptoms associated with menopause, or menopause-related vasomotor symptoms, include at least hot flashes, hot flushes and night sweats in a female perimenopausal, premature menopausal, menopausal, or post menopausal subject, or in a male subject experiencing one or more menopausal-related vasomotor symptoms for any reason.

The term "somnolence" refers to sleepiness, or the state of feeling drowsy.

The term "dosage form" refers to the physical formulation of a drug for administration to the patient. Dosage forms include without limitation, tablets, capsules, caplets, liquids, syrups, lotions, lozenges, aerosols, patches, enemas, oils, ointments, pastes, powders for reconstitution, sachets, solutions, sponges, and wipes. Dosage forms may include non-disintegrating controlled release oral dosage forms comprising a semipermeable membrane as described in U.S. Patent Publication No. 2007/0184104, the disclosure of which is incorporated herein by reference. Within the context of the present methods, a GABA analog dosage form in preferred embodiments is an orally administrable tablet or capsule that swells after administration to a size sufficient for retention in the stomach in the fed mode.

The term "dosage unit" refers to a single unit of the dosage form that is to be administered to the patient. The dosage unit will be typically formulated to include an amount of drug sufficient to achieve a therapeutic effect with a single administration of the dosage unit although where the size of the dosage form is at issue, more than one dosage unit may be necessary to achieve the desired therapeutic effect. For example, a single dosage unit of a drug is typically, one tablet, one capsule, or one tablespoon of liquid. More than one dosage unit may be necessary to administer sufficient drug to achieve a therapeutic effect where the amount of drug causes physical constraints on the size of the dosage form. For example, within the context of the gastric retentive gabapentin dosage form of the present methods, where the therapeutic effective amount of gabapentin is 1800 mg, the patient would be required to take multiple dosage units of gabapentin because a single dosage unit of 1800 mg of gabapentin would be too large for a patient to swallow without discomfort. In such a situation, the patient would take three 600 mg tablets or capsules or two 900 mg tablets or capsules of the gabapentin in order to achieve the 1800 mg therapeutic dose. It is to be understood that the dosage units of the gastric retentive gabapentin described herein is not restricted to any particular size dosage unit (such as the 600 and 900 mg tablets or capsules discussed above) and that any dosage unit of a size that would not be restrictive for comfortable ingestion is contemplated. As an alternative to administering a plurality of 300-900 mg tablets or capsules, a large dose of gabapentin could be prepared in a single large dosage unit that is cut in half at the time of administration. Thus, with the 1800 mg therapeutic dose, a tablet of 1800 mg could be prepared that could be cut in half or in thirds in order to make the 1800 mg dosage unit more easily ingested.

Administration of the dosage form according to the present methods is to a subject in a "fed mode." The fed mode is induced by nutritive elements immediately after food ingestion, and begins with a rapid and profound change in the motor pattern of the upper gastrointestinal (GI) tract, the change occurring over a period of 30 seconds to one minute. During the fed mode the pyloric opening narrows, allowing the stomach to retain particles exceeding about 1 cm in size for approximately 4 to 6 hours. The fed mode can also be induced pharmacologically by the administration of pharmacological agents that have an effect that is the same or similar to that of a meal. These fed-mode inducing agents may be administered separately or they may be included in the dosage form as an ingredient dispersed in the dosage form or in an outer immediate release coating. Examples of pharmacological fed-mode inducing agents are disclosed in U.S. Pat. No. 7,405,238 entitled "Pharmacological Inducement of the Fed Mode for Enhanced Drug Administration to the Stomach," the contents of which are incorporated herein by reference.

Administration of a dosage form "with a meal" or "during or after a meal" refers to administration before, during or after a meal, and more particularly refers to administration of a dosage form about 1, 2, 3, 4, 5, 10, 15 minutes before commencement of a meal, during the meal, or about 1, 2, 3, 4, 5, 10, 15 minutes after completion of a meal.

"Hormone replacement therapy" (HRT) is also referred to as "menopausal hormone therapy" (HT) and includes systemic estrogen therapy (ET or ERT) and estrogen-progestin therapy (EPT). HRT may also include the use of an androgen, in which case it is referred to as estrogen, progesterone and androgen therapy (EPAT).

The term "compliance" as used herein refers to the act of taking medication at a recommended dosage and according to a recommended dosing schedule.

II. Methods of Treatment

In one aspect, methods for alleviating vasomotor symptoms, particularly hot flashes, in a subject are provided. Hot flashes are experienced in male and female subjects for a variety of reasons, including drug treatment, hormonal changes, thyroid disease, infection, and the like. In the methods described herein, a GABA analog is administered to the subject experiencing undesired vasomotor symptoms in the form of an orally administered gastric retentive dosage form. As will be described below, a GABA analog administered in such a dosage form was surprisingly effective in decreasing both the severity and the frequency of undesired vasomotor symptoms, thereby providing an effective method for improving patient compliance in GABA analog treatment in subjects experiencing undesired vasomotor symptoms, improving sleep quality of subjects experiencing hot flashes, treating a post-menopausal female at risk of cardiovascular disease who is experiencing vasomotor symptoms, and treating a female experiencing vasomotor symptoms who is contraindicated for hormone replacement therapy. These and other contemplated methods of treatment are described hereinbelow.

A. Treatment of Menopause-Related Vasomotor Symptoms

The periods of life known as perimenopause and menopause are accompanied in many women by a range of symptoms, including vasomotor symptoms, vulvovaginal atrophy, sexual dysfunction, and mood disturbances. In addition, some women continue to experience symptoms associated with hormonal changes long after menopause, i.e., in the post-menopausal period. Hot flashes are a more common symptom, and because they can be particularly bothersome, are a main focus of menopausal treatment guidelines. Hot flashes are often categorized as mild, moderate, or severe. The methods described herein are suitable for treatment of hot flashes in any or all of these categories.

Accordingly, in one aspect, a method for treating, alleviating, attenuating or modulating hot flashes in a perimenopausal or menopausal female is provided. The female suffering from hot flashes is administered a gastric retentive dosage form comprising a GABA analog, and the dosage form is described in detail below. Examples 1 and 2 describe a study where women experiencing hot flashes were given gabapentin in a gastric retentive dosage form. Administration of gabapentin to this patient population in a gastric retentive dosage form provided a marked reduction in the frequency and/or severity of hot flashes, as evidenced by the data presented herein.

In another aspect, a method for treating, alleviating, attenuating or modulating hot flashes in women postmenopausal for two years or more is provided. Approximately 30% of postmenopausal women experience hot flashes for 5 years after natural menopause and approximately 20% experience hot flashes for 15 years. Due to the fact that risk factors associated with hormone replacement therapy and estrogen-replacement therapy increase over time as the female ages, it is desirable to provide non-hormonal therapies that alleviate or treat the hot flashes and that may be administered over extended periods of time. Administration of a GABA analog in a gastric retentive dosage form to women post-menopausal for 2 years or more and continuing to experience hot flashes is contemplated for treating hot flashes.

B. Methods for Improving Sleep Quality in Subjects

Subjects experiencing hot flashes at night will often experience difficulty sleeping, leading to fatigue and lethargy during the day. Treating night time hot flashes, or night sweats, poses unique challenges, since the treatment regimen preferably reduces day time hot flashes yet allows the subject to remain fully alert and functional during the day, and is sufficient to alleviate night sweats. Accordingly, in another aspect, a method for improving quality of sleep at night in subjects experiencing night sweats and/or hot flashes, with minimal daytime somnolence is provided. In the studies described in Examples 1 and 2, it was unexpectedly found that administering a GABA analog in a gastric retentive dosage form to subjects experiencing hot flashes and night sweats was effective in improving quality of sleep while also minimizing daytime somnolence.

Improvements in sleep quality in a subject may be measured using the Pittsburgh Sleep Quality Index (PSQI) (see FIGS. 1A-1D). The PSQI provides a subjective measure of sleep quality and patterns and is a validated instrument for assessment of sleep quality treatment intervention (Buysse D J et al. "The Pittsburgh Sleep Quality Index: a new instrument for psychiatric practice and research," *Psychiatry Res* 1989: 28(2): 193-213; Smyth, C A, "Evaluating Sleep Quality in Older Adults," *Amer. J. Nursing,* 2008, 108(5):42-50). The PSQI is a self-administered questionnaire which includes four open-ended questions and 14 questions to be answered using event-frequency and semantic scales. This tool looks at subjective sleep quality, sleep latency (the time it takes to fall asleep), sleep duration, habitual sleep efficiency (the ratio of total sleep time to time in bed), sleep disturbances, the use of sleep-promoting medication (prescribed or over-the-counter), and daytime dysfunction. The PSQI is widely accepted as having high validity and reliability as a result of numerous studies using the PSQI in a variety of populations (Knutson K L et al., "Stability of the Pittsburgh Sleep Quality Index and the Epworth Sleepiness Questionnaires over one year in early middle-aged adults: the CARDIA study," *Sleep,* 2006:29(11):1503-1506).

Subjects treated according to methods described herein, using a gastric retentive dosage form of a GABA analog, experience increased quality of sleep during the night, as measured by the PSQI.

C. Methods for Increasing Patient Compliance

Patient compliance in terms of drug administration is a recognized problem in medicine. Patients do not comply with recommended dosing schedules for a variety of reasons, including a dislike of taking medication, a fear of adverse side effects, forgetfulness, and a lack of confidence in the efficacy of the medication. As the number of daily administrations increase, patient compliance is likely to decrease. For a generally healthy patient population such as women or men having hot flashes, adverse side effects can particularly discourage compliance with drug therapy.

In another embodiment of the present invention, gastric retentive dosage forms comprising a GABA analog may be used to provide optimal therapeutic support to a subject by increasing compliance with a long-term dosing regime. Immediate release GABA analog dosage forms may result in increased adverse side effects as compared to the adverse side effects observed in patients dosed with gastric retentive GABA analog dosage forms. This reduction in adverse side effects may lead to increased compliance among patients dosed with gastric retentive gabapentin. Increased compliance results from the reduced number of gabapentin dose administrations required in a single day. In one embodiment, a gastric retentive gabapentin dosage form is administered once per day. In another embodiment, a gastric retentive gabapentin dosage form is administered twice per day.

In some embodiments, the long-term dosing regime is about 3, 4, 5, 6, 7, 8, 9, 10, 11, or 12 months. In some embodiments, the long-term dosing regime is greater than 12 months.

D. Methods for Treating Women at Risk of Cardiovascular Disease or Contraindicated for Hormone Replacement Therapy Cardiovascular disease is a major cause of morbidity in postmenopausal women. Up to the age of 50 years, the prevalence of coronary artery disease in women is lower than in men, but the incidence rises significantly after menopause and continues to increase with aging (Mattar C. N. et al., "Menopause, Hormone Therapy and Cardiovascular and Cerebrovascular Disease," Annals Acad. Medicine, 2008:37 (1):55-62). While the evidence regarding postmenopausal hormone therapy and cardiovascular risk is widely divergent, there are more consistent data showing an increased risk in the incidence of venous thromboembolism and stroke.

Accordingly, in another aspect, a method for treating women who are experiencing hot flashes and who are at risk of cardiovascular disease, venous thromboembolism and/or stroke is provided. The women are treated with a gastric retentive dosage form of a GABA analog, to alleviate the hot flashes. It will be appreciated that the subject can be any female, perimenopausal, menopausal, or postmenopausal, experiencing hot flashes and at risk of cardiovascular disease, for example due to heredity. In one embodiment, the subject is a female who experiences vasomotor symptoms five years or more after undergoing menopause.

In another aspect, a method for treating women experiencing hot flashes and contraindicated for hormone replacement therapy is contemplated. Hormone replacement therapy is a widely used treatment for relief of menopause-associated vasomotor symptoms and is considered the standard of care for women with moderate-to-severe vasomotor symptoms. Hormone replacement therapy involves administration of artificial hormones, including estrogens, progesterone or progestins to the subject. However, hormone replacement therapy is not recommended for certain subjects due to potential serious adverse effects, such as increased risk of endometrial cancer in a female with a uterus if estrogen is taken without progesterone, slightly increased risk of breast cancer after four or more years of hormone replacement therapy, increased breast density, making mammograms more difficult to interpret and possibly increasing breast cancer risk, slightly increased risk of heart attack or stroke, slightly increased risk of ovarian cancer, slightly increased risk of blood clots or gallbladder disease, primarily associated with oral estrogens, breast pain, nausea, bloating and fluid retention, and negative effects on mood.

Thus, a treatment method is provided, where subjects contraindicated for hormone replacement therapy and experiencing hot flashes are treated with a GABA analog in the form of a gastric retentive dosage form. The subjects contraindicated for hormone replacement therapy may include those who have experienced stroke, recent heart attack, a history of breast, endometrial or uterine cancer, acute liver disease, gall bladder disease, pancreatic disease, blood clots or hypertension, undiagnosed vaginal bleeding, and/or pre-menstrual syndrome-type symptoms including breast pain and tenderness. In other embodiments, subjects contraindicated for HRT may include those who smoke or have smoked cigarettes, or have experienced benign breast or uterine disease, endometriosis, pancreatitis, epilepsy, and/or migraine headaches.

E. Methods for Treating Women During a Suspension of Hormone Replacement Therapy Menopausal women, including women experiencing premature menopause, perimenopausal women, and post-menopausal women, who are on hormonal replacement therapy to control the symptoms of menopause are periodically withdrawn from the hormone therapy to determine if their body still requires exogenous hormones (e.g., estrogen). During these periods when hormonal therapy is suspended, patients may experience a return or rebound of their hot flashes in direct response to the withdrawal of exogenous estrogen.

Accordingly, in another aspect, a method of treating a subject who is undergoing a withdrawal in hormone replacement therapy is provided. In a further aspect, a method of treating a subject who is undergoing a permanent halting of hormone replacement therapy is provided. The method comprises administering to the subject a dosage form as described herein, according to any one or more of the dosing regimens or total daily dosages. In some embodiments, the method comprises beginning administration of the dosage form to the subject 1 day, 2 days, 3 days, 4 days, 5 days, 6 days, 7 days, 2 weeks, or 3 weeks prior to the withdrawal from hormone therapy. In some embodiments, the method comprises beginning the administration of the dosage form on the same day that hormone replacement therapy is withdrawn, suspended, or halted. In some embodiments, the method comprises beginning administration of the dosage form to the subject 1 day, 2 days, 3 days, 4 days, 5 days, 6 days, 7 days, 2 weeks, or 3 weeks after the withdrawal from hormone therapy. In some embodiments, the withdrawal from hormone therapy may last from one day to one year, from 5 days to 6 months, from 1 week to 5 months, from 1 week to 4 months, from 1 week to 3 months, from 1 week to 2 months, from 1 week to 1 month, for 1 month, for 2 months, for 3 months, for 5 months or for 6 months.

III. Gastric Retentive Dosage Forms

Gastric retentive oral dosage forms comprising a GABA analog for use in the methods and dosing regimens described and claimed herein have been described elsewhere, for example, in U.S. Pat. Nos. 7,438,927 and 6,723,340, and U.S. Patent Publication Numbers 2007/0184104 and 2003/0104062, all of which are incorporated by reference herein.

Gastric retentive oral dosage forms are preferably comprised of swellable hydrophilic polymers that imbibe fluid upon ingestion by a subject. Upon fluid imbibition, these gastric retentive dosage forms swell to a size large enough such that they cannot easily escape through the pylorus into the small intestine while the subject is in a fed mode. In a preferred embodiment, subjects experiencing hot flashes are administered a gastric retentive dosage form comprising a GABA analog while in the fed mode.

The swellable nature of the gastric retentive dosage forms is due to the properties and ratios of hydrophilic polymers used in the dosage form. For example, the gastric retentive dosage form can contain polymers with a high swelling capacity such as polyethylene oxide, hydroxyethylcellulose, and hydroxypropylmethylcellulose (HPMC). The polymers are preferably of a moderate to high molecular weight ($4 \times 10^3$ Daltons to greater that $1 \times 10^7$ Daltons) to enhance swelling and provide control of the release of the GABA analog. The molecular weight of the polymer may be selected based upon viscosity of the polymer in solution. For example, the polymer may be selected such that a 1% aqueous solution has a viscosity in a range of 100 cps (centipoise) to greater than 100,000 cps. Examples of such polymers include, by way of illustration and not limitation, polymers with a high swelling capacity such as polyethylene oxide ("PEO"), hydroxyethylcellulose, and hydroxypropylmethylcellulose ("HPMC" also known as hypromellose). Examples of suitable PEO polymers are those having molecular weights (viscosity average) on the order of 2-10 million Daltons.

A hydroxypropylmethylcellulose polymer of such molecular weight may be utilized so that the viscosity of a 1% aqueous solution is about 100 cps to greater than 100,000 cps. An example of suitable polyethylene oxide polymers are those having molecular weights (viscosity average) on the order of 2-7 million Daltons.

In a preferred dosage form, a polymer matrix is comprised of PEO and HPMC and the GABA analog is dispersed within the polymer matrix to form a single, solid matrix that swells in an unrestrained and/or unrestricted manner in the presence of water as a single, intact polymer matrix—that is, the polymer matrix does not break into multiple individual particles, but remains as a single polymer matrix for release of the GABA analog by diffusion, erosion or a combination of erosion and diffusion. A preferred polymer matrix comprised of poly(ethylene oxide) and hydroxypropylmethylcellulose is described in detail in U.S. Pat. No. 6,723,340 to Gusler et al., incorporated by reference herein.

A typical dosage form should swell to approximately 115% of its original volume within one hour after administration, and at a later time should swell to a volume that is 130% or more of the original volume.

The gastric retentive GABA analog dosage forms administered according to the methods described herein can be made by techniques that are well established in the art, including wet granulation, fluid-bed granulation, dry granulation, direct compression, and so forth. An example of manufacture of a gastric retentive dosage form in set forth in Example 1.

In addition to the active agent and the polymers, the gastric retentive GABA analog dosage forms may also include additional excipients, which are known to those of skill in the art to which the invention pertains; such excipients may include, for example, binders, lubricants, diluents, fillers, glidants, and other additives. Examples of binders that may be used to formulate the dosage forms include by way of illustration and not limitation, HPMC, hydroxypropylcellulose ("HPC"), methylcellulose ("MC"), microcrystalline cellulose ("MCC"), ethyl cellulose, polyethylene glycol ("PEG"), polyvinylpyrrolidone ("PVP" also known as povidone), vinylpyrolidone-vinyl acetate copolymer (also known as copovidone), polyvinylalcohol ("PVA"), gelatin, starch, and gums.

Examples of lubricants that may be used to formulate the dosage forms include by way of illustration and not limitation, magnesium stearate, calcium stearate, glyceryl behenate, hydrogenated vegetable oils, PED, sodium stearyl fumarate, stearic acid, stearyl behenate, and talc. Gastric retentive GABA analog dosage forms may be formulated using a dry blend process or standard granulation with, for example, magnesium stearate as a lubricant.

Examples of diluents that may be used to formulate the dosage forms include by way of illustration and not limitation, calcium sulfate, cellulose, dicalcium phosphate, kaolin, lactose, mannitol, MCC, sodium chloride, sorbitol, starch, and sucrose. Fillers may include dicalcium phosphate ("DCP"), MCC, spray-dried lactose, maltose, starch, sugars, sugar alcohols, and waxes; glidants may include colloidal silicon dioxide and talc; and other additives may include coloring agents, flavoring agents, sweeteners, and solubility retarding agents.

The GABA analogs or derivatives used in the treatment methods and in the dose titration regimen described above include analogs of gamma-aminobutyric acid. Such analogs include gabapentin (2-[1-(aminomethyl)cyclohexyl]acetic acid), pregabalin ((S)-3-(aminomethyl)-5-methylhexanoic acid), vigabatrin (4-aminohex-5-enoic acid), and baclofen (4-amino-3-(4-chlorophenyl)butanoic acid), which are 3'-alkylated GABA analogs. Additional GABA analogs that may be used are described in Silverman et al., PCT Publication No. WO 92/09560; Silverman et al., PCT Publication No. WO 93/23383; Horwell et al., PCT Publication No. WO 97/29101, Horwell et al., PCT Publication No. WO 97/33858; Horwell et al., PCT Publication No. WO 97/33859; Bryans et al., PCT Publication No. WO 98/17627; Guglietta et al., PCT Publication No. WO 99/08671; Bryans et al., PCT Publication No. WO 99/21824; Bryans et al., PCT Publication No. WO 99/31057; Belliotti et al., PCT Publication No. WO 99/31074; Bryans et al., PCT Publication No. WO 99/31075; Bryans et al., PCT Publication No. WO 99/61424; Bryans et al., PCT Publication No. WO 00/15611; Bryans, PCT Publication No. WO 00/31020; Bryans et al., PCT Publication No. WO 00/50027; and Bryans et al., PCT Publication No. WO 02/00209). New classes of GABA analogs, which are bicyclic amino acid derivatives, have been recently described by Bryans et al., PCT Publication No. WO 01/28978; Blakemore et al., PCT Pub. No. WO 02/085839; Blakemore et al., U.S. Pat. No. 5,596,900; and Blakemore et al., PCT Pub. No. WO 02/090318. In a preferred embodiment, the GABA analog is gabapentin or pregabalin.

The gastric retentive dosage forms described herein provide a drug delivery profile such that a GABA analog, both on an in vivo and in vitro basis, is delivered for at least 5 hours and more typically over a time period of about 8-10 hours. In order to provide for sustained delivery, it is preferable that at least 40 wt % of a GABA analog is retained in the dosage form after 1 hour, i.e., no more than 60 wt % of the drug is administered in the first hour. In addition, it may be desired to utilize a dosage form that provides for substantially all of the GABA analog to be delivered over the intended duration, which is typically about 6-12 hours, where substantially all is taken to mean at least about 85 wt % (generally the art teaches that substantially all is 80 wt %) of the GABA analog is administered.

The dosage form may be a single-layer or a bilayer tablet. Where the dosage form is a bilayer tablet, one layer is the active agent containing layer that releases the gabapentin while the other layer is a swelling or floating layer.

The gastric retentive dosage form of a GABA analog used according to the methods and dose titration regimen described herein may be an extended release oral drug dosage form which releases a GABA analog into the stomach and/or upper small intestine of a patient, which comprises a single solid polymeric particle comprising a GABA analog or a pharmaceutically acceptable salt thereof dispersed within the polymeric particle (or matrix) that (i) swells unrestrained dimensionally by imbibing water from gastric fluid to increase the size of the matrix to promote gastric retention in the stomach of the patient in which the fed mode has been induced; (ii) gradually the GABA analog diffuses or the polymer matrix erodes over a time period of hours, where the diffusion or erosion commences upon contact with the gastric fluid; and (iii) releases the GABA analog to the stomach of the patient, as a result of the diffusion or polymeric erosion at a rate corresponding to the time period.

In a further embodiment, a dosage form is formulated to have a size that achieves prolonged retention in the stomach without swelling. That is, the dosage form prior to administration is sized to have at least one dimension of the dosage form larger than the pyloric opening so that the dosage form is retained in the stomach, and need not swell to achieve retention. Such a dosage form would contain at least 800 mg of a GABA analog, such as gabapentin, and typically 800-1200 mg of drug. Materials and techniques useful for manufacturing these large-sized dosage forms are described in REMINGTON: THE SCIENCE AND PRACTICE OF PHARMACY, 20$^{th}$ edition (Lippincott Williams & Wilkins, 2000) and Ansel et al., PHARMACEUTICAL DOSAGE FORMS AND DRUG DELIVERY SYSTEMS, 6$^{th}$ Ed. (Media, Pa.: Williams & Wilkins, 1995).

These large-sized dosage forms can have, in some embodiments, an outer polymer coating that surrounds the inner drug core. The outer coating is typically formed of a polymer, such as cellulose, cellulose acetate, cellulose acetate butyrate, and ethyl cellulose. Along with the GABA analog, the core of the dosage form may contain pharmaceutically acceptable additives or excipients to facilitate manufacturing. These include binders (e.g., ethyl cellulose, gelatin, gums, polyethylene glycol, polyvinylpyrrolidone, polyvinylalcohol, starch, sugars, waxes), coloring agents, diluents (e.g., calcium sulfate, cellulose, dicalcium phosphate, kaolin, lactose, mannitol, microcrystalline cellulose, sodium chloride, sorbitol, starch, sucrose), flavoring agents, glidants (e.g., colloidal silicon dioxide, talc), and lubricants (e.g., calcium stearate, glyceryl behenate, hydrogenated vegetable oils, magnesium stearate, polyethylene glycol, sodium stearyl fumarate, stearic acid, stearyl behenate, talc). The core may also contain pharmaceutically acceptable additives or excipients that serve to provide desirable physical characteristics to the dosage form. These include sweeteners, polymers, waxes, and solubility-retarding materials.

In a further embodiment, there is provided a method of treating a subject experiencing vasomotor symptoms using a dosage form that may have a drug-containing core surrounded by a swellable coating, as described in U.S. Patent Publication 2003/0104062 which is incorporated by reference herein.

IV. Dosing Regimen

In another aspect, a dosing regimen for use in any of the treatment methods described above is provided. In the dosing regimen, gastric retentive dosage forms comprising a GABA analog is administered to a subject experiencing menopause-related vasomotor symptoms one, two, three, or more times per day when the subject is in a fed mode. Administration to a subject in a fed mode is generally accomplished by oral administration of the dosage form before, during or after a meal. The fed mode is induced by nutritive elements immediately after food ingestion. During the fed mode, indigestible particles greater in size than the pyloric opening are retropelled and retained in the stomach. The stomach thus retains particles exceeding about 1 cm in size for a prolonged period of time, for example, approximately 4 to 6 hours.

In one embodiment, subjects are dosed with the gastric retentive GABA analog once per day, with a morning, noontime, or evening meal. A once-daily dosing regimen may comprise administration of the gastric retentive GABA analog dosage form in the evening with an evening meal or in the morning with a morning meal. Alternatively, subjects may be administered a gastric retentive GABA analog dosage form twice per day. A twice-daily dosing regimen may comprise, for example, administration of the gastric retentive GABA analog in the evening with an evening meal and in the morning with a morning meal.

With the twice-daily dosing regimen, the two dosings may be administered in a symmetric or asymmetric dosing regimen. In a symmetric dosing regimen, the morning dose is the same as the evening dose. As an example, a symmetric dosing regimen may consist of 600 mg of gabapentin in the morning and 600 mg of gabapentin in the evening for a total daily dose of 1200 mg of gabapentin for a single 24 hour period. With gabapentin, symmetric dosing regimens are best used where lower dosages of gabapentin are being used for treating a particular disease state or condition.

With the twice-daily dosing regimen in an asymmetric dosing regimen, the morning and evening doses are not be the same. Where high doses of gabapentin are being used to treat a particular subject, asymmetric dosing regimens are preferred. Examples of asymmetric dosing regimens include, 300 mg in the morning and 1200 mg in the evening for a total daily dose of 1500 mg/day; 600 mg in the morning and 1200 mg in the evening for a total daily dose of 1800 mg/day; 600 mg in the morning and 1800 mg in the evening for a total daily dose of 2400 mg; 1200 mg in the morning and 1800 mg in the evening for a total daily dose of 3000 mg; 600 mg in the morning and 3600 mg in the evening for a total daily dose of 4200 mg/day; or 900 mg in the morning and 6000 mg in the evening for a total daily dose of 6900 mg/day.

By way of example, in one embodiment a method of treating a subject experiencing vasomotor symptoms such as hot flashes or hot flushes comprises administering a total daily dose of gabapentin ranging from about 300 mg/day to about 3600 mg/day, from about 600 mg/day to about 3000 mg/day, from about 1200 mg/day to about 2400 mg/day, from about 600 mg/day to about 1800 mg/day, from about 300 mg/day to about 1200 mg/day, from about 600 mg/day to about 1200 mg/day. In some embodiments, the method comprises administering a total daily dose of gabapentin of about 300 mg, about 600 mg, about 900 mg, about 1200 mg, about 1500 mg, about 1600 mg, about 1800 mg, about 2000 mg, about 2400 mg, about 3000 mg, or about 3600 mg.

In some embodiments, a method of treating a subject experiencing vasomotor symptoms such as hot flashes or hot flushes comprises administering a total daily dose of pregabalin ranging from about 25 mg/day to about 500 mg/day. Examples of total daily doses of pregabalin include approximately 25, 50, 75, 100, 125, 150, 175, 200, 225, 250, 275, 300, 325, 350, 375, 400, 425, 450, 475, or 500 mg/day.

In another aspect, a dose titration regimen for treating a subject experiencing menopause-related vasomotor symptoms is provided. In the dose titration regimen, a total daily dose of a GABA analog is administered as a gastric retentive dosage form is varied during the first 1-7 days of treatment followed by an extended period of treatment with a total daily dose which is less than, equal to, or greater than the daily dose administered during the first 1-7 days. Such dose titration regimens may be useful, for example, in reducing adverse effects upon initiation of treatment in any of the treatment methods described herein.

Where the total daily dose of gabapentin is 1000 mg or greater, the subject is preferably titrated up to the maximum maintenance dose that the patient is capable of tolerating. Titration is preferable with both the once-daily and twice-daily dosing regimens.

Dose titration is the process of gradually adjusting the dose of a medication until the desired effect is achieved. It is done in part to monitor and reduce incidence of adverse side effects. Depending on the medication, dose titration may be a lengthy and complex process. Some medications require no titration. In the present methods, a gastric retentive GABA analog dosage form is administered to a subject experiencing menopause-related vasomotor symptoms. When a dose titration regimen is implemented, dosing over the first 1-7 days of the treatment period may be less than that administered in the following days of treatment.

A dose titration regimen for treating a subject experiencing vasomotor symptoms including hot flashes or hot flushes may comprise administering a first daily dose for a first period of time, for example, for one, two or three days. The dose titration regimen further comprises a second daily dose that is administered for a second period of time, for example, three, four, or five days. A third daily dose may optionally then be administered for one, two or three days and may be less than, equal to, or greater than the second daily dose. After a dose titration period of about seven days, a treatment period follows comprising administration of a daily dose administered during the treatment period may be less than, equal to, or greater than the second or third daily dose. The treatment period may last for 2-25 weeks, or for 1, 2, 3, 4, 5, 6, 7, 8, 9, 10, 11, 12 or more months.

The first, second, and third daily doses described herein refer to the total amount of a GABA analog administered in a 24-hour period. Each daily dose may be administered in one, two, or more administrations of a unit dosage form comprising an amount of a GABA analog. Each administration may comprise oral administration of one, two or more gastric retentive dosage units. For example, a total daily dose of 1800 mg GABA analog may be administered twice-daily in which 600 mg is administered with a morning meal and 1200 mg is administered with an evening meal. Administration of 1200 mg gabapentin could be accomplished, for example, by administration of two 600 mg gabapentin dosage units, or by administration of four 300 mg gabapentin dosage units.

In an exemplary embodiment, a dose titration regimen for treating a subject experiencing vasomotor symptoms comprises administering 600 mg of the gastric retentive gabapentin dosage form to the subject in the evening with an evening meal for days 1 and 2. The subject is then administered 1200 mg of the gastric retentive gabapentin dosage form with an evening meal for days 3-7. After this first week, the subject is then administered 1200 mg of the gastric retentive gabapentin dosage form with an evening meal for weeks 2-25.

A dose titration regimen employed to prepare a subject for twice-daily dosing may comprise, for example, a first daily dose of 600 mg of the gastric retentive gabapentin administered to a subject in the evening with an evening meal for days 1 and 2, a second daily dose of 1200 mg of the gastric retentive gabapentin administered to a subject in the evening with an evening meal for days 3, 4 and 5, and a third daily dose of 1800 mg of the gastric retentive gabapentin administered to a subject in the evening with an evening meal for days 6 and 7, in which 600 mg gabapentin is administered in the morning with a morning meal and 1200 mg gabapentin is administered in the evening with an evening meal. After day 7, the subject is administered 1800 mg/day gastric retentive gabapentin twice per day, with 600 mg administered in the morning with a morning meal and 1200 mg gabapentin is administered in the evening with an evening meal. This dosing regimen may occur for several weeks, months, or years.

In some cases, a subject may experience adverse events during the dose titration. In this situation, the dose titration regimen may be altered. For example, the first and/or second daily doses may be administered for additional days.

All patent applications, patents, publications, and other published documents mentioned or referred to in this specification are incorporated herein by reference in their entireties, to the same extent as if each individual patent application, patent, publication, and other published document was specifically and individually indicated to be incorporated by reference.

IV. Examples

The treatment methods described herein are further described with reference to the following examples which are intended to enable those skilled in the art to more clearly understand and to practice the treatment methods. The following examples are not intended, nor are they to be construed, as limiting the scope of the methods, but are merely intended to be illustrative and representative of the methods.

Example 1

A Multicenter, Randomized, Double-Blind, Placebo-Controlled Study of the Pharmacokinetics and Pharmacodynamics of Gastric Retentive Gabapentin Dosage Form in the Treatment of Hot Flashes in Postmenopausal Women A. Preparation of Gabapentin Gastric Retentive Dosage Forms and Placebo Tablets Gabapentin gastric retentive tablets containing 300 milligrams (mg) or 600 mg of gabapentin (Teva-Tech Ltd, Beer-Sheva, 84874 Israel) were prepared with the components shown in Tables 1A-1C below. The gastric retentive tablets were prepared in an isopropanol-based high-shear granulation with 31.6 mg of copovidone per tablet as a binder. In preparing the 600 mg tablets, this granulation was subsequently blended with 258.4 mg per tablet of high molecular weight polyethylene oxide (Sentry™ POLYOX™ 303), and 100 mg/tablet of hypromellose (Methocel® K15M) as swelling and rate-controlling polymers, with 10 mg magnesium stearate as a lubricant. This blend was compressed into 1000 mg tablets with modified oval B tooling of a shape "0.4330× 0.7450." These tablets were subsequently coated with 20 mg of Opadry® II white.

TABLE 1A

Qualitative Composition of Gabapentin Gastric Retentive Tablets

| Component | Description/Function | Reference to Standard |
|---|---|---|
| Gabapentin | Active | USP |
| Excipients: | | |
| Polyethylene Oxide, FP NF [SENTRY ™ POLYOX ™ WSR-303 FP NF; DOW Chemical Co.] | Swelling, Controls Release | NF |
| Hypromellose, USP, type 2208 [Methocel ® K15M, premium; Dow Chemical Co.] | Swelling, Controls Release | USP |
| Copovidone, EP [Kollidon, VA 64; BASF Corporation] | Binder | EP |
| Opadry ® II White (85G1490) [Colorcon Corp.] | Film coating, aesthetics | Depomed Standard |
| Microcrystalline Cellulose, NF* [Avicel ® PH-101; FMC Biopolymer] | Binder | NF |
| Magnesium Stearate, NF, Non-Bovine, USP, EP [Mallinckrodt] | Tablet lubricant | NF, USP, EP |
| Purified Water, USP/EP | Coating solution solvent | USP, EP |
| Isopropyl Alcohol [2-Propanol] USP, EP | Granulation solvent | USP, EP |

*Microcrystalline Cellulose, NF is included only in the 300 mg formulation

TABLE 1B

Gabapentin GASTRIC RETENTIVE Tablets, 300 mg formulation

| Ingredient | % w/w | mg/Tablet |
|---|---|---|
| Uncoated Tablet | | |
| Gabapentin | 42.857% | 300.00 |
| Polyethylene Oxide NF [Sentry ™ Polyox ™ WSR 303 FP NF Grade] | 22.000% | 154.00 |
| Hypromellose, USP/EP (2208) [Methocel K15M Premium] | 20.000% | 140.00 |
| Microcrystalline Cellulose, NF, EP [Avicel PH-101] | 11.886% | 83.2 |
| Copovidone, EP [Kollidon VA 64] | 2.257% | 15.8 |
| Magnesium Stearate NF, Non-Bovine, USP, EP | 1.000% | 7.0 |
| Isopropyl Alcohol [2-Propanol], USP/EP* | — | — |
| Total: | 100.00% | 700.0 |
| Coated Tablet | | |
| Gabapentin gastric retentive tablet, 300 mg, uncoated | 98.04% | 700.00 |
| Opadry II, White [85G18490]** | 1.96% | 14.0** |
| Purified Water, USP/EP* | — | — |
| Total: | 100.00% | 714.0 |

*Removed during drug product manufacturing
**2.0% of uncoated tablet weight

TABLE 1C

Gabapentin Gastric Retentive Tablets, 600 mg formulation

| Ingredient | % w/w | mg/Tablet |
|---|---|---|
| Uncoated Tablet | | |
| Gabapentin | 60.00% | 600.0 |
| Polyethylene Oxide NF [Sentry ™ Polyox ™ WSR 303 FP NF Grade] | 25.84% | 258.4 |

TABLE 1C-continued

Gabapentin Gastric Retentive Tablets, 600 mg formulation

| Ingredient | % w/w | mg/Tablet |
|---|---|---|
| Hypromellose, USP/EP (2208) [Methocel K15M Premium] | 10.00% | 100.0 |
| Copovidone, EP [Kollidon VA 64] | 3.16% | 31.6 |
| Magnesium Stearate NF, Non-Bovine, USP, EP | 1.00% | 10.0 |
| Isopropyl Alcohol [2-Propanol], USP/EP* | — | — |
| Total: Coated Tablet | 100.00% | 1000.0 |
| Gabapentin gastric retentive tablet, 600 mg, uncoated | 98.04% | 1000.00 |
| Opadry II, White [85G18490]** | 1.96% | 20.0** |
| Purified Water, USP/EP* | — | — |
| Total: | 100.00% | 1020.0 |

*Removed during the drug product manufacturing
**2.0% of uncoated tablet weight

Placebo tablets were identical visually to the active gabapentin tablets, but were comprised of lactose instead of gabapentin, polyethylene oxide, microcrystalline cellulose, and magnesium stearate.

B. Method of Treatment

A multicenter randomized, double-blind clinical trial was conducted in postmenopausal women of ≧18 years of age who reported ≧7 severe hot flashes per day over the previous 30 days or longer. Specifically, the study enrolled 124 postmenopausal women (approximately 30 per group) with recurrent, moderate to severe hot flashes (mean approximately 10 per day), and was conducted at eight sites in the United States. A total of 123 patients received randomized therapy with 107 completing all efficacy periods of the study. Four patients in each group withdrew from the study.

The patients were randomized into four groups A-D (Table 2 shown below) with the first three groups (Groups A, B, C) receiving two periods of active treatment each lasting for six weeks. Group D received placebo tablets throughout the entire study. All patients receiving active treatments had a one week dose titration period, a five-week fixed dose treatment period, a second one-week dose titration period, and a second five-week fixed dose treatment period. Blood samples were taken over a 24-hour period after the first dose during titration and at the end of treatment weeks 6 and 12, for pharmacokinetic analysis. Patients recorded the occurrence and severity of hot flashes in an electronic diary during a 1-week baseline period and throughout the study. Patients were instructed to take the medication with breakfast and with dinner. The study dosing schedule for each group was as shown in Table 2 below:

TABLE 2

Dosing Regimen for Treatment Groups

| | Titration 1 (Week 1) | Weeks 2-6 | Titration 2 (Week 7) | Weeks 8-12 |
|---|---|---|---|---|
| Group A | To 600 mg | 600 mg PM | To 1800 mg | 600 mg AM + 1200 mg PM |
| Group B | To 1200 mg | 600 mg AM + 600 mg PM | To 2400 mg | 600 mg AM + 1800 mg PM |
| Group C | To 1200 mg | 1200 mg PM | To 3000 mg | 1200 mg AM + 1800 mg PM |
| Group D | Placebo | Placebo | Placebo | Placebo |

A pharmacokinetic analysis of the dosage form was obtained by determining the blood plasma concentrations of gabapentin at selected time points during the treatment period, and a pharmacodynamic analysis was done by evaluating the frequency and severity of hot flashes in the patients at regular time points during the treatment period. Quality of sleep was also assessed using the Pittsburgh Sleep Quality Index (PSQI). Safety was assessed by the incidence and severity of adverse reactions (AEs).

Primary efficacy measures included changes in daily frequency and in average daily severity score of moderate to severe hot flashes from baseline to the final week of the treatment period. Secondary endpoints included mean changes in average daily frequency and in average daily severity score of moderate to severe hot flashes from baseline to week six (6) of the efficacy treatment period, percent change in average daily frequency and in average daily severity score of moderate to severe hot flashes from baseline to the final week of the efficacy treatment period, and 75% responder rate.

The overall effect of treatment as rated by Patient Global Impression of Change (PGIC) and by Investigator-rated Clinical Global Impression of Change (CGIC) were evaluated at week six (6) and at the final week of the treatment period. Mean change in PSQI scores from baseline to week four (4) and week ten (10) was also measured.

The Patient Global Impression of Change is a 0-10 scale for patients to use in rating the degree of improvement they have experienced since beginning treatment. A two (2) point change is required to demonstrate a significant level of improvement. The patient's score is simply the rating value selected. A rating of zero (0) represents a great deal of improvement. A rating of ten (10) represents a significant worsening of the patient's perceived condition. A rating of five (5) indicates no perceived change. The Clinical Global Impression of Change rating scales are commonly used measures of symptom severity, treatment response and the efficacy of treatments in treatment studies of patients with mental disorders. The Clinical Global Impression-Improvement scale (CGI-I) is a 7 point scale that requires the clinician to assess how much the patient's illness has improved or worsened relative to a baseline state at the beginning of the intervention and rated as: 1, very much improved; 2, much improved; 3, minimally improved; 4, no change; 5, minimally worse; 6, much worse; or 7, very much worse.

A summary of the efficacy results of this study are shown in Table 3. The average daily frequency and daily total severity score were reduced substantially at endpoint (Week 12), compared to baseline, in the 1800 mg b.i.d. group, compared to the placebo group. Clinical Global Impression of Change ratings of much improved or very much improved were reported for 83.3%, 77.8%, 73.3%, and 53.6% of patients treated with Gabapentin GR™ 1800 mg, 2400 mg, 3000 mg, and placebo, respectively. PGIC ratings of much improved or very much approved were reported by 83.3%, 77.8%, 70.8%, and 58.6% of patients treated with G-ER 1800 mg, 2400 mg, 3000 mg, and placebo, respectively.

TABLE 3

Summary of Phase 2 Efficacy Results for Hot Flashes

| Moderate-to-severe Hot Flashes: | Gabapentin GR ™ 1800 mg (N = 30) LS Mean (SEM) | P | Gabapentin GR ™ 2400 mg (N = 30) LS Mean (SEM) | P | Gabapentin ™ GR 3000 mg (N = 32) LS Mean (SEM) | P | Placebo (N = 30) LS Mean (SEM) |
|---|---|---|---|---|---|---|---|
| Change from baseline in daily frequency | −8.12 (0.70) | 0.016* | −7.89 (0.70) | 0.030* | −6.90 (0.67) | 0.229 | −5.74 (0.69) |
| Percent change | −73.32% (6.12) | 0.029* | −69.96% (6.11) | 0.072 | −62.75% (5.9) | 0.325 | −54.41% (6.11) |
| Responder %. | 63.30% | 0.039* | 50.00% | 0.299 | 56.30% | 0.122 | 36.70% |
| Change from baseline in daily severity score | −0.78 (0.16) | 0.167 | −0.87 (0.16) | 0.072 | −0.73 (0.15) | 0.228 | −0.47 (0.16) |
| Percent change | −33.08% (6.61) | 0.12 | −34.70% (6.60) | 0.085 | −31.21% (6.3) | 0.169 | −18.61% (6.60) |
| Responder % | 26.70% | 0.095 | 30.00% | 0.053 | 21.90% | 0.203 | 10.00% |
| ##Change from baseline in average daily total severity score | −19.77 (1.87) | 0.044* | −19.86 (1.87) | 0.041* | −16.51 (1.80) | 0.426 | −14.47 (1.85) |
| Very much or much improved (CGIC) | 83.30% | 0.015* | 77.80% | 0.059 | 73.30% | 0.119 | 53.60% |
| Very much or much improved (PGIC) | 83.30% | 0.036* | 77.80% | 0.124 | 70.00% | 0.361 | 58.60% |
| Change from baseline in PSQI (Week 10): | | | | | | | |
| Subjective sleep quality | −0.70 (0.14) | 0.102 | −0.78 (0.14) | 0.041* | −0.91 (0.14) | 0.007* | −0.38 (0.14) |
| Sleep disturbance | −0.42 (0.11) | 0.038* | −0.45 (0.11) | 0.021* | −0.34 (0.11) | 0.112 | −0.10 (0.11) |

*P < 0.05 compared with placebo
LS: Least squares
SEM: standard error of the LS mean
Average daily severity score = [(Number of moderate hot flashes × 2) + (number of severe hot flashes × 3)]/Total daily number of moderate to severe hot flashes
Average daily total severity score = (Number of moderate hot flashes × 2) + (number of severe hot flashes × 3)

One null hypothesis tested in the study was that the treatment difference of the least squares ("LS") mean change in the average daily frequency of moderate to severe hot flashes (imputed by last observation carried forward ("LOCF")) from baseline to the final week of the efficacy treatment period between each Gabapentin gastric retentive treatment group and the placebo treatment group was zero. All statistical tests were performed at the $\alpha$=0.05 significance level. A parallel lines analysis of covariance ("ANCOVA") model was used for the analysis of the primary efficacy measurements, and this model included treatment, center, treatment-by-center interaction factor, and baseline average daily frequency or severity as the covariate.

The analysis of the LOCF average daily hot flash frequency for the second treatment period is shown in Table 4. Gabapentin gastric retentive dosage forms administered at dosages of 1800 mg AM/PM and 2400 mg AM/PM exhibited statistically greater reductions in the daily frequency of hot flashes compared to placebo. Patients treated with gabapentin gastric retentive dosage forms administered at a dosage of 3000 mg AM/PM displayed larger reductions in hot flash frequency compared to placebo, although non-statistical likely due to outliers in the group. At the lower doses in the first treatment period shown in Table 5, the treatment groups receiving 600 mg PM, 1200 mg AM/PM and 1200 mg PM exhibited trends, which were not statistically different, toward greater reductions in the frequency of hot flashes.

TABLE 4

Analysis of LOCF Average Daily Frequency of Moderate to Severe Hot Flashes at Endpoint: Intent-to-Treat Population (Parallel Model)

| Moderate to Severe Hot Flashes (HF) | Treatment Group | | | | Overall Treatment p-value [1] |
|---|---|---|---|---|---|
| | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | |
| Baseline | | | | | |
| n | 30 | 30 | 32 | 30 | 0.268 |
| Mean (SD) | 9.92 (2.28) | 11.62 (4.64) | 11.31 (3.53) | 10.46 (3.53) | |
| LS Mean (SEM) | 10.10 (0.66) | 11.76 (0.66) | 11.42 (0.64) | 10.63 (0.66) | |
| 95% CI | (8.80, 11.41) | (10.45, 13.06) | (10.15, 12.68) | (9.32, 11.93) | |
| p-value (vs. Placebo) [2] | 0.572 | 0.223 | 0.385 | | |
| Endpoint | | | | | |
| n | 30 | 30 | 32 | 30 | 0.063 |
| Mean (SD) | 2.31 (2.51) | 2.97 (2.89) | 3.89 (4.99) | 4.87 (4.37) | |
| LS Mean (SEM) | 2.72 (0.70) | 2.95 (0.70) | 3.94 (0.67) | 5.09 (0.69) | |
| 95% CI | (1.34, 4.10) | (1.57, 4.33) | (2.60, 5.27) | (3.72, 6.46) | |

TABLE 4-continued

Analysis of LOCF Average Daily Frequency of Moderate to Severe
Hot Flashes at Endpoint: Intent-to-Treat Population (Parallel Model)

| Moderate to Severe Hot Flashes (HF) | Treatment Group | | | | Overall Treatment p-value [1] |
|---|---|---|---|---|---|
| | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | |
| Change from Baseline to Endpoint | | | | | |
| n | 30 | 30 | 32 | 30 | 0.063 |
| Mean (SD) | −7.61 (3.40) | −8.65 (5.70) | −7.42 (5.82) | −5.60 (3.17) | |
| LS Mean (SEM) | −8.12 (0.70) | −7.89 (0.70) | −6.90 (0.67) | −5.74 (0.69) | |
| 95% CI | (−9.50, −6.74) | (−9.27, −6.50) | (−8.23, −5.57) | (−7.11, −4.37) | |
| P-value (W) [3] | <0.001 | <0.001 | <0.001 | <0.001 | |
| Gabapentin ER minus Placebo | | | | | |
| LS Mean Difference (SEM) | −2.37 (0.97) | −2.14 (0.98) | −1.16 (0.96) | NA | |
| 95% CI for Difference | (−4.30, −0.45) | (−4.08, −0.21) | (−3.05, 0.74) | | |
| p-value (vs. Placebo) [2] | 0.016 | 0.030 | 0.229 | | |

Note:
Patients who had both baseline and endpoint are included in this data analysis.
LOCF = Last observation carried forward
LS = Least squares;
SEM = standard error of LS mean;
CI = Confidence interval;
NA = Not applicable
For the baseline value, the LS mean and SEM are estimated from the ANOVA model that includes treatment and center factors.
For the endpoint and the change from baseline to endpoint value, the LS mean and SEM are estimated from the ANCOVA model that includes treatment and center factors, and baseline value as a covariate.
[1] The p-value (overall) for the overall comparison among all treatment groups is based on Type III analysis from the models described above.
[2] The p-value (vs. Placebo) for the pair-wise test of difference of the LS mean change from baseline between Gabapentin ER and placebo groups is based on the t-test of Type III analysis from the models described above.
[3] The p-value (W) for the test of LS mean change from baseline within treatment group is based on the t-test of Type III analysis from the models described above

TABLE 5

Analysis of LOCF Average Daily Frequency of Moderate to Severe Hot Flashes by Week:
Intent-to-Treat Population

| Moderate to Severe Hot Flashes | Treatment Group | | | | Overall Treatment p-value [1] |
|---|---|---|---|---|---|
| | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | |
| Week 6 | | | | | |
| n | 30 | 30 | 32 | 30 | 0.356 |
| Mean (SD) | 4.03 (4.32) | 4.30 (3.60) | 4.57 (5.16) | 5.78 (4.50) | |
| LS Mean (SEM) | 4.51 (0.80) | 4.19 (0.80) | 4.53 (0.77) | 6.03 (0.80) | |
| 95% CI | (2.92, 6.10) | (2.60, 5.78) | (2.99, 6.06) | (4.45, 7.61) | |
| Change from Baseline to Week 6 | | | | | |
| n | 30 | 30 | 32 | 30 | 0.356 |
| Mean (SD) | −5.89 (4.80) | −7.32 (5.65) | −6.74 (5.44) | −4.68 (3.36) | |
| LS Mean (SEM) | −6.33 (0.80) | −6.64 (0.80) | −6.31 (0.77) | −4.81 (0.80) | |
| 95% CI | (−7.92, −4.74) | (−8.23, −5.05) | (−7.84, −4.78) | (−6.38, −3.23) | |
| P-value (W) [3] | <0.001 | <0.001 | <0.001 | <0.001 | |
| Gabapentin ER minus Placebo | | | | | |
| LS Mean Difference (SEM) | −1.52 (1.12) | −1.84 (1.12) | −1.50 (1.10) | NA | |
| 95% CI for Difference | (−3.73, 0.69) | (−4.06, 0.39) | (−3.68, 0.68) | | |
| p-value (vs. Placebo) [2] | 0.176 | 0.105 | 0.175 | | |

Note:
Patients who had both baseline and endpoint are included in this data analysis.
LOCF = Last observation carried forward
LS = Least squares;
SEM = standard error of LS mean;
CI = Confidence interval;
NA = Not applicable TABLE 5-continued Analysis of LOCF Average Daily Frequency of Moderate to Severe Hot Flashes by Week: Intent-to-Treat Population

| Moderate to Severe Hot Flashes | Treatment Group | | | | Overall Treatment p-value [1] |
|---|---|---|---|---|---|
| | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | |

For the baseline value, the LS mean and SEM are estimated from the ANOVA model that includes treatment and center factors.
For the weekly follow-up and the change from baseline to weekly follow-up value, the LS mean and SEM are estimated from the ANCOVA model that includes treatment and center factors, and baseline value as a covariate.
[1] The p-value (overall) for the overall comparison among all treatment groups is based on Type III analysis from the models described above.
[2] The p-value (vs. Placebo) for the pairwise test of difference of the LS mean change from baseline between Gabapentin ER and placebo groups is based on the t-test of Type III analysis from the models described above.
[3] The p-value (W) for the test of LS mean change from baseline within treatment group is based on the t-test of Type III analysis from the models described above.

The analysis of the LOCF average daily hot flash severity score for the second treatment period is shown in Table 6. Patients treated with gabapentin gastric retentive dosage forms at doses of 1800 mg AM/PM and 2400 mg AM/PM exhibited statistically greater reductions in the daily severity of hot flashes compared to placebo. The patients receiving gabapentin in a gastric retentive dosage form at a dose of 3000 mg AM/PM group displayed larger reductions in hot flash severity compared to placebo, although the reduction was not statistically significant due to outliers in the treatment group. For patients receiving lower doses in the first treatment period, shown in Table 7, the patients treated with gabapentin in a gastric retentive dosage form at a dose of 600 mg PM, 1200 mg AM/PM or 1200 mg PM exhibited trends, which were not statistically different, toward greater reductions in the severity of hot flashes.

TABLE 6

Analysis of LOCF Average Daily Severity Score of Moderate to Severe Hot Flashes at Endpoint: Intent-to-treat Population (Parallel Model)

| Moderate to Severe Hot Flashes (HFC) | Treatment Group | | | | Overall Treatment p-value [1] |
|---|---|---|---|---|---|
| | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | |
| Baseline | | | | | |
| n | 30 | 30 | 32 | 30 | 0.200 |
| Mean (SD) | 23.51 (6.22) | 29.30 (13.59) | 27.47 (9.91) | 26.33 (9.96) | |
| LS Mean (SEM) | 24.00 (1.89) | 29.62 (1.89) | 27.76 (1.83) | 26.73 (1.89) | |
| 95% CI | (20.26, 27.75) | (25.88, 33.36) | (24.14, 31.38) | (22.99, 30.47) | |
| p-value (vs. Placebo) [2] | 0.305 | 0.277 | 0.694 | | |
| Endpoint | | | | | |
| n | 30 | 30 | 32 | 30 | 0.108 |
| Mean (SD) | 5.52 (6.80) | 7.09 (7.14) | 9.96 (14.50) | 11.73 (11.28) | |
| LS Mean (SEM) | 6.90 (1.87) | 6.81 (1.87) | 10.16 (1.80) | 12.20 (1.85) | |
| 95% CI | (3.19, 10.61) | (3.10, 10.52) | (6.60, 13.72) | (8.53, 15.87) | |
| Change from Baseline to Endpoint | | | | | |
| n | 30 | 30 | 32 | 30 | 0.108 |
| Mean (SD) | −17.99 (9.08) | −22.21 (15.99) | −17.51 (15.00) | −14.60 (8.54) | |
| LS Mean (SEM) | −19.77 (1.87) | 19.86 (1.87) | −16.51 (1.80) | −14.47 (1.85) | |
| 95% CI | (−23.48, −16.06) | (−23.57, −16.15) | (−20.07, −12.95) | (−18.14, −10.79) | |
| P-value (W) [3] | <0.001 | <0.001 | <0.001 | <0.001 | |
| Gabapentin ER minus Placebo | | | | | |
| LS Mean Difference (SEM) | −5.30 (2.61) | −5.39 (2.61) | −2.04 (2.56) | NA | |
| 95% CI for Difference | (−10.47, −0.13) | (−10.57, −0.22) | (−7.11, 3.03) | | |
| p-value (vs. Placebo) [2] | 0.044 | 0.041 | 0.426 | | |

Note:
Patients who had both baseline and endpoint are included in this data analysis.
LOCF = Last observation carried forward
LS = Least squares;
SEM = standard error of LS mean;
CI = Confidence interval;
NA = Not applicable
For the baseline value, the LS mean and SEM are estimated from the ANOVA model that includes treatment and center factors.
For the endpoint and the change from baseline to endpoint value, the LS mean and SEM are estimated from the ANCOVA model that includes treatment and center factors, and baseline value as a covariate.
[1] The p-value (overall) for the overall comparison among all treatment groups is based on Type III analysis from the models described above.

TABLE 6-continued

Analysis of LOCF Average Daily Severity Score of Moderate to Severe
Hot Flashes at Endpoint: Intent-to-treat Population (Parallel Model)

|  | Treatment Group | | | | |
| --- | --- | --- | --- | --- | --- |
| Moderate to Severe Hot Flashes (HFC) | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | Overall Treatment p-value [1] |

[2] The p-value (vs. Placebo) for the pair-wise test of difference of the LS mean change from baseline between Gabapentin ER and placebo groups is based on the t-test of Type III analysis from the models described above.
[3] The p-value (W) for the test of LS mean change from baseline within treatment group is based on the t-test of Type III analysis from the models described above.

TABLE 7

Analysis of LOCF Average Daily Severity Score of Moderate to Severe Hot Flashes by Week
Intent-to-treat Population

| Moderate to Severe Hot Flashes Score | Treatment Group | | | | |
| --- | --- | --- | --- | --- | --- |
|  | Gabapentin ER 1800 mg (AM/PM) (n = 30) | Gabapentin ER 2400 mg (AM/PM) (n = 30) | Gabapentin ER 3000 mg (AM/PM) (n = 32) | Placebo (n = 30) | Overall Treatment p-value [1] |
| Week 6 | | | | | |
| n | 30 | 30 | 32 | 30 | 0.572 |
| Mean (SD) | 9.68 (12.41) | 10.55 (9.25) | 12.00 (15.42) | 13.75 (11.26) | |
| LS Mean (SEM) | 11.30 (2.21) | 9.94 (2.21) | 11.96 (2.12) | 14.19 (2.18) | |
| 95% CI | (6.93, 15.67) | (5.57, 14.31) | (7.76, 16.15) | (9.86, 18.51) | |
| Change from Baseline to Week 6 | | | | | |
| n | 30 | 30 | 32 | 30 | 0.572 |
| Mean (SD) | −13.82 (13.77) | −18.75 (15.81) | −15.48 (13.90) | −12.57 (8.91) | |
| LS Mean (SEM) | −15.37 (2.21) | −16.73 (2.21) | −14.71 (2.12) | −12.48 (2.18) | |
| 95% CI | (−19.74, −11.00) | (−21.10, −12.36) | (−18.90, −10.52) | (−16.80, −8.15) | |
| P-value (W) [3] | <0.001 | <0.001 | <0.001 | <0.001 | |
| Gabapentin ER minus Placebo | | | | | |
| LS Mean Difference (SEM) | −2.89 (3.07) | −4.25 (3.07) | −2.23 (3.01) | NA | |
| 95% CI for Difference | (−8.98, 3.20) | (−10.34, 1.84) | (−8.20, 3.74) | | |
| p-value (vs. Placebo) [2] | 0.349 | 0.169 | 0.460 | | |

Note:
Patients who had both baseline and endpoint are included in this data analysis.
LOCF = Last observation carried forward
LS = Least squares;
SEM = standard error of LS mean;
CI = Confidence interval;
NA = Not applicable
For the baseline value, the LS mean and SEM are estimated from the ANOVA model that includes treatment and center factors.
For the weekly follow-up and the change from baseline to weekly follow-up value, the LS mean and SEM are estimated from the ANCOVA model that includes treatment and center factors, and baseline value as a covariate.
[1] The p-value (overall) for the overall comparison among all treatment groups is based on Type III analysis from the models described above.
[2] The p-value (vs. Placebo) for the pair-wise test of difference of the LS mean change from baseline between Gabapentin ER and placebo groups is based on the t-test of Type III analysis from the models described above.
[3] The p-value (W) for the test of LS mean change from baseline within treatment group is based on the t-test of Type III analysis from the models described above.

In the treatment group at 1800 mg AM/PM, the LS mean number of moderate-to-severe hot flashes was reduced from 10.1 at baseline to 2.7 at endpoint (p=0.016) and from 11.8 to 3.0 (p=0.03) in the 2400 mg treatment group, compared to LS mean baseline value of 10.9 and an endpoint value of 5.1 for the placebo group (see Table 4). A statistically greater decrease of at least 80% in the frequency of moderate-to-severe hot flashes was observed in 63% of patients in the 1800 mg treatment arm, compared to 20% of placebo patients.

As shown below in Table 8, gabapentin at a dose of 1800 mg in a gastric retentive dosage form was well tolerated with a low incidence of dizziness and somnolence.

TABLE 8

Adverse Effects

| Most common side effects | 1800 mg | 2400 mg | 3000 mg | Placebo |
| --- | --- | --- | --- | --- |
| Headache | 32% | 32% | 25% | 10% |
| Somnolence | 16% | 16% | 16% | 3% |
| Dizziness | 10% | 39% | 9% | 10% |

The study demonstrates that gabapentin administered in a gastric retentive dosage form is effective for the treatment of hot flash symptoms in postmenopausal women and was well tolerated with a low incidence of the typical side effects of gabapentin.

Example 2

A Multicenter, Randomized, Double-Blind, Placebo-Controlled Study of the Safety and Efficacy of Gabapentin Extended Release Tablets in the Treatment of Vasomotor Symptoms in Postmenopausal Women The gabapentin gastric retentive dosage form and placebo tablets are prepared as described in Example 1.

The primary objective of this study is to assess the efficacy of gabapentin administered in a gastric retentive dosage form for the treatment of women experiencing hot flashes. The patients in the study are treated with one of two daily dosing regimens: 1) 1200 mg gabapentin in a gastric retentive dosage form, administered in the evening with an evening meal, or 2) 600 mg gabapentin in a gastric retentive dosage form, administered in the morning with a morning meal and 1200 mg gabapentin in a gastric retentive dosage form, administered in the evening with an evening meal, for a total daily dose of 1800 mg gabapentin. A matching placebo group for each dosing regimen was included, in which the patients received placebo tablets each evening or each morning and evening to match the dosing patterns of the treatment groups.

Each one of the treatment periods was preceded by up to seven days of titration to reach the patient's assigned dose or placebo equivalent, where the full seven day titration period was permitted for patients who, in the opinion of the investigator, experienced significant adverse events.

Two studies are carried out to determine efficacy of gabapentin administered in the above two dosing regimens from a gastric retentive dosage form for the treatment of hot flashes: a 3-month study and a 6-month study. Each study begins with a one-week period to establish a baseline of hot flash frequency and severity for each patient. Subjects who experience an average of seven (7) or more moderate to severe hot flashes per day or about fifty (50) per week, are randomized into treatment and placebo groups. A sample size of approximately 540 patients is intended for each study to ensure that at least 471 patients (157 per treatment group) completed treatment and have available efficacy data for analysis.

Following establishment of a baseline, enrolled patients underwent a one-week dose titration regimen, as outlined in Table 9 below.

TABLE 9

Dose Titration Regimen for Administration of Gabapentin Gastric Retentive Dosage Forms

| Study Day | Group A<br>1200 PM | Group B<br>600 AM/1200 PM | Group C<br>PLACEBO |
| --- | --- | --- | --- |
| Titration Period | | | |
| Day 1, 2 | —/600 | —/600 | —/0 |
| Day 3, 4, 5 | —/1200 | —/1200 | —/0 |
| Days 6, 7 | 0/1200 | 600/1200 | 0/0 |
| Treatment weeks 2-25 or 2-13 | 0/1200 | 600/1200 | 0/0 |

Patients who experience adverse effects follow a modified dose titration regimen outlined in Table 10.

TABLE 10

Dose Titration Regimen for Administration of Gabapentin Gastric Retentive Dosage Form Tablets in Patients Experiencing Adverse Side Effects

| Study Day | Group A<br>1200 PM | Group B<br>600 AM/1200 PM | Group C<br>PLACEBO |
| --- | --- | --- | --- |
| Titration Period | | | |
| Day 1, 2, 3 | —/600 | —/600 | —/0 |
| Day 4, 5, 6, 7 | —/1200 | —/1200 | —/0 |
| Treatment weeks 2-13 or 2-25 | 0/1200 | 600/1200 | 0/0 |

Following the one-week dose titration regimen, patients receive a fixed dose of gabapentin in a gastric retentive dosage form for 12 weeks (treatment weeks 2-13) in the 3-month study, or for 24 weeks (treatment weeks 2-25) in the 6-month study. Accordingly, treatment in the 3-month study is for a total period of 13 weeks and treatment in the 6-month study is for a total period of 25 weeks. The 3-month and 6-month studies is the same in all other aspects, such as the dose titration regimen, dosing regimen during the post-titration treatment period, and methods of assessing efficacy.

For the fixed-dose treatment period in the 3-month study, subjects in Group A receive 1200 mg gabapentin in a gastric retentive dosage form once daily with an evening meal for treatment weeks 2-13. Subjects in Group B receive gabapentin twice daily –1200 mg gabapentin in a gastric retentive dosage form with an evening meal and 600 mg gabapentin in the same dosage form with a morning meal.

In the 6-month study, subjects in Group A receive 1200 mg gabapentin in a gastric retentive dosage form once daily with an evening meal for weeks 2-25. Subjects in Group B receive gabapentin twice daily –1200 mg gabapentin in a gastric retentive dosage form with an evening meal and 600 mg gabapentin in a gastric retentive dosage form with a morning meal.

Both the 3-month and 6-month studies include a placebo group, Group C, with patients that receive placebo gastric retentive dosage forms.

Efficacy Measurements

A primary outcome measure is the reduction in frequency and severity of hot flashes after 12 weeks and 24 weeks of treatment with a fixed dose of gabapentin administered in a gastric retentive dosage form relative to placebo, compared to the baseline week, for the 3-month and 6-month studies, respectively. Patients are provided with definitions of mild, moderate, and severe hot flashes to self-evaluate hot flashes as they occur. Mild hot flashes are defined as a sensation of heat without sweating, moderate hot flashes are defined as a sensation of heat with sweating, but ability to continue current activity, and severe hot flashes are defined as a sensation of heat with sweating such that current activity ceased.

Secondary endpoints that are measured include (i) reduction of frequency and severity of hot flashes after treatment with a stable dose relative to placebo, compared with the baseline week, (ii) changes from baseline in sleep quality as measured by the Pittsburgh Sleep Quality Index (PSQI; see FIGS. 6A-6D) evaluated at Randomization, Week 5, Week 13, and, for the 6-month study, Week 25, (iii) quality of life as assessed by the Menopause-Specific Quality of Life Questionnaire (MENQOL; see FIGS. 2A-2E) evaluated at Randomization, Week 5, Week 13, and Week 25, and (iv) overall effect of treatment as rated by Patient Global Impression of Change (PGIC) and by Investigator-rated Clinical Global Impression of Change (CGIC) evaluated at Week 13 and Week 25 end of treatment visits for the 3-month and 6-month studies, respectively. The MENQOL is a validated instrument for assessment of change in menopause related quality of life following treatment intervention (Hilditch J R et al. "A menopause-specific quality of life questionnaire: development and psychometric properties. *Maturitas,* 1996, 24(3):161-175).

An electronic diary (DiaryPRO) is used by each patient from the beginning of the baseline week to the end of the treatment period to record information about each hot flash as it is experienced. The DiaryPRO is a Palm Pilot device that allows patients to record the occurrence and severity of each hot flash event in real time. There is an the opportunity to add any unrecorded events each morning to capture events that happen during the night when the patient may not record the event in real time.

Subjects are assessed at scheduled visits to occur at Week 1 (End of Titration), Week 5, Week 9, Week 13 (End-of-Treatment for 3-month study), Week 10, and Week 25 (End of Treatment for 6-month study). During each visit, the information on each patient's DiaryPRO is uploaded at the site to allow tracking of the frequency and severity of hot flashes, as well as patient compliance with diary completion. Patients are also queried on the occurrence of any adverse events. MENQOL and PSQI questionnaires are completed during visits for weeks 0 (end of the baseline week, prior to randomization), 5 and 13. Patients in the 6-month study also complete MENQOL questionnaires during the end-of-treatment visit (week 25).

Adverse Events

Safety is assessed by the incidence and severity of adverse events (AEs), analysis of clinical laboratory values for chemistry and hematology, vital signs, physical examination findings, and the use of concomitant medications.

Physical examinations and vital signs are monitored at Weeks 1, 5, 9, 13, 19 and 25. Height and weight are measured at screening, and weight is measured at Week 13 and Week 25, or at any early termination visits. At screening and end-of-study/early termination visits, hematology tests is done to measure hemoglobin, hematocrit, red blood cell (RBC) count, and white blood cell (WBC) count, including differential leukocyte count and platelet count. In addition, standard blood chemistry tests is done to measure albumin, total protein, sodium, potassium, blood urea nitrogen (BUN), creatinine, serum glutamic oxaloacetic transaminase (SGOT) serum glutamate pyruvate transaminase (SGPT), alkaline phosphatase, gamma glutamyl transferase, total bilirubin, triglyceride, total cholesterol, lactate dehydrogenase (LDH), calcium, uric acid, estradiol, and FSH.

Adverse event monitoring includes any noxious, pathological, or unintended change in anatomical, physiological, or metabolic functions as indicated by physical signs, symptoms, and/or laboratory changes occurring in any phase of the study, whether or not associated with the administered medication or placebo. Adverse severity is defined as mild if the event is noticeable to the patient, but does not influence the patient's daily activities. The adverse event is moderate if it results in slight discomfort and the patient's activities are influenced. The adverse event is considered severe if it results in severe discomfort for the patient and usually interferes with the patient's daily activities.

Analysis of Efficacy Data

The primary efficacy parameters are derived from data collected from the daily diary. Mean change in last observation carried forward (LOCF) average daily frequency of moderate to severe hot flashes is determined for the period from the baseline week to the fourth and twelfth weeks of the stable dose efficacy treatment period. Mean change in LOCF average daily severity score of moderate to severe hot flashes is determined for the period from the baseline week to the fourth and twelfth weeks of the stable dose efficacy treatment period. The daily severity score is the sum of individual severity score of all moderate to severe hot flashes adjusted by the daily frequency of moderate to severe hot flashes reported during a specific day. The severity scores of moderate and severe hot flashes are 2 and 3, respectively.

The secondary efficacy parameters to be analyzed include the mean change in observed and LOCF average daily frequency of moderate to severe hot flashes from the baseline week to the final week of the efficacy treatment period and the mean change in observed and LOCF average daily severity score of moderate to severe hot flashes from the baseline week to the final week of the efficacy treatment period. Also measured is the proportion of patients who had a 75% or greater reduction in average daily frequency of moderate to severe hot flashes from baseline to LOCF endpoints, and the proportion of patients who had a 75% or greater reduction in average daily severity score of moderate to severe hot flashes from baseline to LOCF endpoints.

In addition, the proportion of patients who are categorized as very much or much improved in Clinical Global Impression of Change at the twelfth week of the stable dose and the final week of the efficacy treatment period are determined, as will the proportion of patients who are categorized as very much or much improved in Patient Global Impression of Change at the twelfth week of the stable dose and the final week of the efficacy treatment period.

Mean change in seven PSQI component scores from baseline (randomization visit) to the fourth and twelfth weeks of the stable dose and the final week of the efficacy treatment period is determined. There are 19 individual items on the PSQI generate seven "component" scores: subjective sleep quality, sleep latency, sleep duration, habitual sleep efficiency, sleep disturbances, use of sleeping medication, and daytime dysfunction. The scores of each of these seven PSQI components are 0, 1, 2, and 3.

Mean change in Pittsburgh Sleep Quality Index global score from baseline to the fourth and twelfth weeks of the stable dose and the final week of the efficacy treatment period is determined. The PSQI global score is the sum of seven "component" scores. The range of the PSQI global score is from 0 to 21.

Mean change in four MENQOL domain scores from baseline (randomization visit) to the fourth and twelfth weeks of the stable dose and the final week of the efficacy treatment period is determined. There are 29 individual items on the MENQOL generate four "domain" scores: vasomotor [3 items (1-3)], psychosocial [7 items (4-10)], physical [16 items (11-26)], and sexual [3 items (27-29)]. Patients are asked whether they have experienced the item in the previous week and answer 'no' or 'yes'. If the answer is 'yes', they indicate how bothered they were on a 7-point Likert scale ranged from '0'='not at all bothered' to '6'='extremely bothered'. The converted scores of each of these MENQOL items range from 1 to 8 for data analysis (1 for 'no', 2 for 'yes and not at all bothered' through to 8 for 'yes and extremely bothered'). The domain score is taken as the mean of the converted item scores forming that domain and ranges from 1 to 8.

Mean change in MENQOL summary score from baseline to the fourth and twelfth weeks of the stable dose and the final week of the efficacy treatment period is determined. The MENQOL summary score is the mean of four domain scores and ranges from 1 to 8.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for improving quality of sleep at night in a subject experiencing vasomotor symptoms, comprising:
   administering to a subject experiencing vasomotor symptoms a twice-daily dose of gabapentin in a dosage form comprising a hydrophilic polymer, wherein after administration the dosage form swells to a size that is retained in the stomach of the subject in a fed mode, and wherein the administering comprises administering a first dose of 600 mg with a morning meal and a second dose of 1200 mg with an evening meal;
   whereby the dose of gabapentin improves the quality of sleep at night in the subject, as measured by the Pittsburgh Quality Sleep Index, relative to a subject experiencing vasomotor symptoms untreated with the dose of gabapentin; and
   wherein the subject experiences minimal daytime somnolence or reduced daytime somnolence relative to somnolence experienced with an immediate release dose of gabapentin.

2. The method of claim 1, wherein the subject experiencing vasomotor symptoms is a female experiencing menopause-related hot flashes.

3. The method of claim 1, wherein the subject is a post-menopausal female experiencing menopause-related vasomotor symptoms who is at risk of cardiovascular disease.

4. The method of claim 1, wherein the subject is a female experiencing menopause-related vasomotor symptoms and contraindicated for hormone-replacement therapy.

5. A dosing regimen for treating a female subject experiencing menopause-related vasomotor symptoms, comprising:
   administering, to a female subject experiencing menopause-related vasomotor symptoms, a first daily dose of gabapentin in a dosage form comprising a hydrophilic polymer, wherein after administration the dosage form swells to a size that is retained in the stomach in a fed mode, the first dose administered for a first time period; and
   administering to said subject a second daily dose of gabapentin, greater than the first dose of gabapentin, in a dosage form comprising a hydrophilic polymer, wherein after administration the dosage form swells to a size that is retained in a stomach in a fed mode, the second dose administered after the first time period, for a second time period;
   wherein said first daily dose and said second daily dose comprise a first dosage form administered with a morning meal and at least a second dosage form administered with an evening meal, the first daily dose and the second daily dose providing a total daily dose of about 1800 mg gabapentin;
   wherein the dosing regimen improves the quality of sleep at night in the subject, as measured by the Pittsburgh Quality Sleep Index, relative to a subject experiencing vasomotor symptoms untreated with the dosage regimen;
   and wherein the subject experiences minimal daytime somnolence or reduced daytime somnolence relative to somnolence experienced with immediate release dosages of gabapentin.

6. The dosing regimen of claim 5, whereby the dosing regimen reduces frequency or severity of the menopause-related vasomotor symptoms.

7. The dosing regimen of claim 5, wherein the second dose of gabapentin is administered for a third period of time.

8. The dosing regimen of claim 5, further comprising administering a third daily dose of gabapentin, less than the second dose of gabapentin, in a dosage form comprising a hydrophilic polymer, wherein after administration the dosage form swells to a size retained in the stomach in the fed mode, the third dose administered after the second time period, for a third time period.

9. The method of claim 5, wherein the first daily dose is 600 mg and wherein the second daily dose is 1200 mg.

10. The method of claim 9, wherein the first period of time is 2 days and the second period is 3 days.

11. A method of improving quality of sleep at night in a female subject experiencing vasomotor symptoms, comprising:
    administering to a female subject experiencing vasomotor symptoms a dosage form comprised of a dosage unit of about 600 mg of gabapentin, wherein the dosage form is formulated to be of a size that is retained in a stomach in a fed mode, said dosage form administered with a morning meal, and
    administering to the subject a second dosage unit of about 1200 mg of gabapentin, said dosage unit in one or more dosage forms formulated to be of a size that is retained in a stomach in a fed mode, said dosage form administered with an evening meal,
    whereby the administering provides an improvement in quality of sleep at night as measured by the Pittsburgh Quality Sleep Index and relative to a female subject experiencing vasomotor symptoms untreated with the dosage form, and whereby the administering either causes minimal daytime somnolence or reduces daytime somnolence as compared to somnolence caused by immediate release gabapentin.

12. The method of claim 1, wherein the subject is withdrawing from hormone replacement therapy.

* * * * *